United States Patent
Chan et al.

(10) Patent No.: US 10,059,736 B2
(45) Date of Patent: *Aug. 28, 2018

(54) IONIC LIQUID SUPPORTED SYNTHESIS

(75) Inventors: Tak-Hang Chan, Toronto (CA); Masad J. Damha, St. Hubert (CA); Weishi Miao, Toronto (CA); Robert Alexander Donga, St-Bruno de Montarville (CA); Xun He, Hockessin (DE)

(73) Assignee: McGill University, Montreal (CA)

( * ) Notice: Subject to any disclaimer, the term of this patent is extended or adjusted under 35 U.S.C. 154(b) by 921 days.

This patent is subject to a terminal disclaimer.

(21) Appl. No.: 11/908,487

(22) PCT Filed: Mar. 15, 2006

(86) PCT No.: PCT/CA2006/000355
§ 371 (c)(1),
(2), (4) Date: Oct. 20, 2009

(87) PCT Pub. No.: WO2006/096963
PCT Pub. Date: Sep. 21, 2006

(65) Prior Publication Data
US 2010/0041869 A1 Feb. 18, 2010

Related U.S. Application Data

(60) Provisional application No. 60/661,480, filed on Mar. 15, 2005.

(51) Int. Cl.
| | |
|---|---|
| *C07H 21/00* | (2006.01) |
| *C07H 3/06* | (2006.01) |
| *C07K 1/02* | (2006.01) |
| *C07K 1/04* | (2006.01) |

(52) U.S. Cl.
CPC ............. *C07H 21/00* (2013.01); *C07H 3/06* (2013.01); *C07K 1/023* (2013.01); *C07K 1/04* (2013.01); *Y02P 20/542* (2015.11)

(58) Field of Classification Search
CPC ....... C07H 21/02; C07H 21/04; C07D 233/08
USPC .............. 530/338; 548/300.1; 536/25.1, 23.1
See application file for complete search history.

(56) References Cited

U.S. PATENT DOCUMENTS

| | | | | |
|---|---|---|---|---|
| 6,969,693 | B2 * | 11/2005 | Sauvage ............. | B01J 31/0295 502/159 |
| 2002/0085964 | A1 | 7/2002 | Seeberger et al. ............. | 422/190 |
| 2003/0083489 | A1 * | 5/2003 | Myerson .............. | C07D 213/20 536/25.3 |
| 2005/0112679 | A1 * | 5/2005 | Myerson et al. .................. | 435/6 |
| 2006/0128996 | A1 * | 6/2006 | Vaultier et al. ............... | 568/312 |
| 2006/0149035 | A1 * | 7/2006 | Rudolph et al. .............. | 530/333 |

FOREIGN PATENT DOCUMENTS

| | | | |
|---|---|---|---|
| WO | 2004/029004 | * | 4/2004 |
| WO | WO 2004/029004 | | 4/2004 |
| WO | WO 2005/005345 | | 1/2005 |

OTHER PUBLICATIONS

Barany (Int J Peptide Protein Res 30, 705-739, 1987).*
Bonora, Gian Maria (Applied Biochemistry and Biotechnology (1995), 54(1-3), 3-17).*
De Kort (Tetrahedron Letters 45, 2171-2175, 2004).*
Donga, Robert A. (Nucleosides, Nucleotides & Nucleic Acids (2007), 26(10-12), 1287-1293).*
Donga, Robert A. (Journal of Organic Chemistry (2006), 71(20), 7907-7910).*
Fraga-Dubreuil (Tetrahedron Letters 42, 6097-6100, 2001).*
Iyer, Radhakrishnan P. (Comprehensive Natural Products Chemistry (1999), vol. 7, 105-152).*
Pfleiderer, Wolfgang (Acta Biochimica Polonica (1996), 43(1), 37-44).*
Vallette (Tetrahedron Letters 45, 1617-1619, 2004).*
Xun, He (Synthesis No. 10, 1645-1651, 2006).*
Fukumoto, J. Am. Chem. Soc. 127, 2398-2399, 2005.*
Alvarado-Urbina et al., "Automated synthesis of gene fragments," *Science*, 214:270-274, 1981.
Anjaiah et al., "Synthesis and preliminary use of novel acrylic ester-derived task-specific ionic liquids," *Tetrahedron Lett.*, 45:569-571, 2004.
Audic et al., "An ionic liquid-supported ruthenium carbene complex: a robust and recyclable catalyst for ring-closing olefin metathesis in ionic liquids," *J. Am. Chem. Soc.*, 125:9248-9249, 2003.
Bayer et al., "Liquid phase synthesis of peptides," *Nature*, 237:512-513, 1972.
Bellon et al., "Oligonucleotide synthesis," *Solid-Phase Synthesis*, pp. 475-528, 2000.
Betzemeier and Knochel, "Palladium-Catalyzed Cross-Coupling of Organozinc Bromides with Aryl Iodides in Perfluorinated Solvents", *Angew. Chem., Int. Ed. Engl.*, 36:2623-2624, 1997.
Bonora et al., "HELP (high efficiency liquid phase) new oligonucleotide synthesis on soluble polymeric support," *Nucleic Acids Res.*, 18:3155-3159, 1990.
Bower et al., "Enkephalin. Synthesis of Two Pentapeptides isolated from Porcine Brain with Receptor-mediated Opiate Agonist Activity", *J. Chem. Soc. Perkins Trans.*, 1:2488-4292, 1976.

(Continued)

*Primary Examiner* — Satyanarayana R Gudibande
(74) *Attorney, Agent, or Firm* — DLA Piper LLP (US)

(57) ABSTRACT

The present invention relates to ionic liquids for use in chemical applications and capable of serving the dual function of solvent and liquid support. The ionic liquid lends itself to a method of synthesizing oligomers selected from the group consisting of oligopeptides, oligosaccharides and oligonucleotides, comprising contacting a first monomer unit with an ionic liquid at reaction conditions to provide an ionic liquid bound monomer unit; and contacting the ionic liquid bound monomer unit with at least one further monomer unit at reaction conditions to provide an ionic liquid bound oligomer comprising from 2 to 30 monomer units. The method lends itself to large scale manufacture of oligopeptides, oligosaccharides and oligonucleotides.

14 Claims, 7 Drawing Sheets

Specification includes a Sequence Listing.

(56) References Cited

OTHER PUBLICATIONS

Caruthers et al., "Chemical synthesis of deoxyoligonucleotides by the phosphoramidite method," *Methods Enzymol.*, 154:287-313, 1987.

Damha et al., "Oligoribonucleotide synthesis. The silylphosphoramidite method," *Methods in Molecular Biology*, 20:81-114, 1993.

De Kort et al., "Development of a novel ionic support and its application in the ionic liquid phase assisted synthesis of a potent antithrombotic," *Tetrahedron Lett.*, 45:2171-2175, 2004.

Douglas et al., Polymer-supported solution phase synthesis of oligosaccharides, *J Am. Chem. Soc.*, 113:5095-5097, 1991.

Douglas et al., "Polymer-Supported Solution Synthesis of Oligosaccharides Using a Novel Versatile Linker for the Synthesis of D-Mannopentaose, a Structural Unit of D-Mannans of Pathogenic Yeasts," *J. Am. Chem. Soc.*, 117:2116, 1995.

Dudkin, et al., "Chemical Synthesis of Normal and Transformed PSA Glycopeptides," *J. Am. Chem. Soc.*, 126, 736, 2004.

Erbeldinger et al., Enzymatic catalysis of formation of Z-Aspartame in ionic liquid—An alternative to enzymatic catalysis in organic solvents, *Biotechnology Progress*, 16:1129-1131, 2000.

Fraga-Dubreuil et al., "Efficient combination of task-specific ionic liquid and microwave dielectric heating applied to one-pot three component synthesis of a small library of 4-thiazolidinones," *Tetrahedron*, 59:6121-6130, 2003.

Fraga-Dubreuil, "Grafted ionic liquid-phase-supported synthesis of small organic molecules," *Tetrahedron Lett.*, 42:6097-6100, 2001.

Gravert and Janda, "Organic Synthesis on soluble Polymer Supports: Liquid-Phase Methodologies," *Chem. Rev.*, 97:489-509, 1997.

Handy et al., "Fructose-derived ionic liquids: recyclable homogeneous supports," *Tetrahedron Lett.*, 44:8399-8402, 2003.

Holbrey et al., "The phase behavior of 1-alkyl-3-methylimidazolium tetrafluoroborates; ionic liquids and ionic liquid crystals", *J. Chem. Soc. Dalton Trans.*, pp. 2133-2140, 1999.

Horvath et al. "Facile Catalyst Separation Without Water: Fluorous Biphase Hydroformylation of Olefins," *J. Science.*, 266:72-75, 1994.

Horvath, "Fluorous biphase chemistry," *Acc. Chem. Res.*, 31:641-650, 1998.

Ito et al., "Intramolecular Aglycon Delivery on Polymer Support: Gatekeeper Monitored Glycosylation," *J. Am. Chem. Soc.*, 119:5562-5566, 1997.

Jaunzems et al., "Solid-Phase-Assisted Solution-Phase Synthesis with Minimum Purification—Preparation of 2-Deoxyglycoconjugates from Thioglycosides", *Angew. Chem. Ind. Ed.*, 42(10):1166-1170, 2003.

Jiang et al., "Use of low molecular weight polyethylene glycol linker for polymer-supported solution synthesis of oligosaccharides", *Chem. Comm.*, pp. 2193-2194, 1996.

Jiang et al., "Regioselective Acylation of Hexopyranosides with Pivaloyl Chloride," *J. Org. Chem.*, 63(17):6035-6038, 1998.

Kimizuka et al., "Spontaneous self-assembly of glycolipid bilayer membranes in super-philic ionic liquid and formation of ionogel," *Langmuir*, 17:6759-6761, 2001.

Law et al., "Formation and reactions of alkylzinc reagents in room-temperature ionic liquids," *J. Org. Chem.*, 70:10434-10439, 2005.

Leone et al., "An ionic liquid form of DNA: redox-active molten salts of nucleic acids," *J. Am. Chem. Soc.*, 123:218-222, 2001.

Letsinger et al., "Nucleotide chemistry, II. Oligonucleotide synthesis on a polymer support," *J. Am. Chem. Soc.*, 87:3526-3527, 1965.

Letsinger et al., "Organoboron compunds. X. Popcorn polymers and highly cross-linked vinyl polymers containing boron," *J. Am. Chem. Soc.*, 81:3009-3012, 1959.

Love et al., "Automated solid-phase synthesis of protected tumor-associated antigen and blood group determinant oligosaccharides," *Angew. Chem. Int. Ed.*, 43:602-605, 2004.

Majumdar et al., "Synthesis of oligosaccharides on soluble high-molecular-weight branched polymers in combination with purification by nanofiltration," *Org. Lett.*, 5:3591-3594, 2003.

Merrifield et al., "Solid Phase Peptide Synthesis I. The synthesis of a tetrapeptide," *J. Am. Chem. Soc.*, 85:2149-2154, 1963.

Miao et al., "Ionic liquid-supported synthesis of small molecules, peptides and other reactions," *230th ACS National Meeting*, Washington, DC, US, Aug. 28-Sep. 1, 2005 ORGN-556, Publisher: American Chemical Society.

Miao et al., "Ionic-liquid-supported peptide synthesis demonstrated by the synthesis of Leu(5)-enkephalin," *J. Org. Chem.*, 70:3251-3255, 2005.

Miao et al., "Exploration of ionic liquids as soluble supports for organic synthesis. Demonstration with a Suzuki coupling reaction.," *Org. Lett.*, 5:5003-5005, 2003.

Miura et al., "Oligosaccharide synthesis on a fluorous support," *Angew. Chem. Int. Ed.*, 42:2047-2051, 2003.

Miura et al., "Fluorous oligosaccharide synthesis using a novel fluorous protective group," *Org. Lett.*, 3:3947-3950, 2001.

Miura et al., "Rapid synthesis of oligosaccharide moieties of globotriaosylceramide using fluorous protective group," *Tetrahedron Lett.*, 44:1819-1821, 2003.

Mizuno et al., "Peptide synthesis on fluorous support," *Tetrahedron Lett.*, 45:3425-3428, 2004.

Ogilvie et al., "Total chemical synthesis of a 77-nucelotide-long RNA sequence having methionine-acceptance activity," *Proc. Natl. Acad Sci. USA.*, 85:5764-5768, 1988.

Osborn et al., "Recent developments in polymer supported syntheses of oligosaccharides and glycopeptides," *Tetrahedron*, 55:1807-1815, 1999.

Plante et al., "Automated solid-phase synthesis of oligosaccharides," *Science*, 291:1523-1527, 2001.

Sears et al., "Toward automated synthesis of oligosaccharides and glycoproteins," *Science*, 291:2344, 2001.

Seeberger et al., "Solid-Phase synthesis of Oligosaccharides and glycoconjugates by the Glycal Assembly method: A Five Year Retrospective", *J. Am. Chem. Res.*, 31:685, 1998.

Sheldon, "Catalytic reactions in ionic liquids", *Chem. Comm.*, pp. 2399-2407, 2001.

Smith et al., "Nonenzymatic synthesis of peptides in an ionic liquid," *Electrochemcial Socieity Proceedings*, 19:268-275, 2002.

Studer et al., "Fluorous Synthesis: A fluorous phase strategy for improving separation efficiency in organic synthesis," *Science*, 275:823-826, 1997.

Toy et al., "Soluble polymer-supported organic synthesis," *Acc. Chem. Res.*, 33:546-554, 2000.

Vallette et al., "Peptide synthesis in room temperature ionic liquids," *Tetrahedron Lett.*, 45:1617-1619, 2004.

Wasserscheid et al., "Ionic Liquids—New 'Solutions' for Transition metal Catalysis", *Angew. Chem. Int. Ed.*, 39:3773-3789, 2000.

Welton et al., "Room-Temperature Ionic Liquids. Solvents for Synthesis and Catalysis<" *Chem. Rev.*, 99:2071, 1999.

Wende et al., "Fluorous catalysis without fluorous solvents: a friendlier catalyst recovery/recycling protocol based upon thermomorphic properties and liquid/solid phase separation," *J. Am. Chem. Soc.*, 123:11490-11491, 2001.

Wende et al., "Fluorous catalysis under homogeneous conditions without fluorous solvents: a "greener" catalyst recycling protocol based upon temperature-dependent solubilities and liquid/solid phase separation," *J. Am. Chem. Soc.*, 125:5861-5872, 2003.

Wentworth et al., "Liquid-phase chemistry: recent advances in soluble polymer-supported catalysts, reagents and synthesis", *Chem. Comm.*, pp. 1917-1924, 1999.

Wilkes, "A short history of ionic liquids—from molten salts to neoteric solvents", *Green Chem.*, 4:73-80, 2002.

Yao et al., "Olefin metathesis in the ionic liquid 1-butyl-3-methylimidazolium hexafluorophosphate using a recyclable Ru catalyst: remarkable effect of a designer ionic tag," *Angew. Chem. Int. Ed.*, 42:3395-3398, 2003.

Zhang, "Fluorous technologies for solution-phase high-throughput organic synthesis," *Tetrahedron*, 59:4475-4489, 2003.

(56) References Cited

OTHER PUBLICATIONS

Seeberger and Hasse, "Solid-Phase Oligosaccharide Synthesis and Combinatorial Carbohydrate Libraries", *Chem. Rev.*, 100:4349-4393, 2000.

Mutter et al., "New Method of Polypeptide Synthesis", *Angew. Chem. Int. Ed.*, 10(11), 811-812, 1971.

Curran et al., "Preparation of a Fluorous Benzyl Protecting Group and Its Use in Fluorous Synthesis Approach to a Disaccharide", *Tetrahedron Letters*, 39:4937-4940, 1998.

Jing and Huang, "Fluorous thiols in oligosaccharide synthesis", *Tetrahedron Letters*, 45:4615-4618, 2004.

Manzoin, "Rapid synthesis of oligosaccharides using an anomeric fluorous silyl protecting group", *Chem. Comm.*, 2930-2931, 2003.

Manzoni and Castelli, "Synthesis of the Lewis a Trisaccharide Based on an Anomeric Silyl Fluorous Tag", *Organic Letters*, 6(23):4195-4198, 2004.

Palmacci et al., "'Cap-Tag'—novel Methods for Rapid Purification of Oligosaccharides Prepared by Automated Solid-Phase Synthesis", *Angew Chem. Int. Ed.*, 40(23):4433-4437, 2001.

Mizuno et al., "A novel peptide synthesis using fluorous chemistry", *Chem. Comm.*, pp. 972-973, 2003.

Sheldon et al., "Biocatalysis in ionic liquids", *Green Chemistry*, 4:147-151, 2002.

Huddleson et al., "Room temperature ionic liquids as novel media for 'clean' liquid-liquid extraction", *Chem. Commun.*, pp. 1765-1766, 1998.

Bosmann et al., "Deep desulfurization of diesel fuel by extraction with ionic liquids", *Chem. Comm.*, pp. 2494-2495, 2001.

Ye et al., "Room-temperature ionic liquids: a novel versatile lubricant", *Chem. Comm.*, pp. 2244-2245, 2001.

Kahne et al., "Glycosylation of Unreactive Substrates",*J. Am. Chem. Soc.*, 111:6881-6882, 1989.

Yan and Kahne, "Generalizing Glycosylation: Synthesis of the Blood Group Antigens Le-a, Le-b, and Le-x Using a Standard Set of Reaction Conditions", *J. Am. Chem. Soc.*, 118:9239-9248, 1996.

Gildersleeve et al., "Sulfenate Intermediates in the Sulfoxide Glycosylation Reaction", *J. Am. Chem. Soc.*, 120:5961-5969, 1998.

Gildersleeve et al, "Scavenging Byproducts in the Sulfoxide Glycosylation Reaction: Aplication to the Synthesis of Ciclamycin 0", *J. Am. Chem. Soc.*, 121:6176-6182, 1999.

Liang et al., "Parallel synthesis and Screening of a solid Phase Carbohydrate Library", *Science*, 274(5292:1520-1522, 1996.

Crich and Sun, "Direct Synthesis of Beta-Mannopyranosides by the Sulfoxide Method", *J. Org. Chem.*, 626:1198-1199, 1997.

Chrich and Smith, "Solid-Phase Synthesis of Beta Mannosides", *JACS*, 124:8867-8869, 2002.

Chrich et al., "Influence of the 4,6-O-Phenyloboronate, and 4,6-O-Polystyrylboronate Protecting Groups on the Stereochemical Outcome of Thioglycoside-Based Glycosylations Mediated by l-Benzenesulfinyl Piperidine/Triflic Anydride and N-Iodosuccinimide/Trimethylsilyl Triflate", *J. Org. Chem.*, 68:8142-8148, 2003.

Garcia et al., "Direct Glycosylations with 1-Hydroxy Glycosyl Donors using Trifluoromethanesulfonic Anhydride and Diphenyl Sulfoxide", *J. Am. Chem. Soc.*, 119:7597-7598, 1997.

Honda and Gin, "C2-Hydroxyglycosylation with Glycal Donors. Probing the Mechanism of Sulfonium-Mediated Oxygen Transfer to Glycal Enol Ethers", *J. Am. Chem. Soc.*, 124:7343-7352, 2002.

Wipf and Reeves, "Glycosylation via Cp2ZrCl2/AgClO4-Mediated Activation of Anomeric Sulfoxides", *J. Org. Chem.*, 66:7910-7914, 2001.

Guillier et al., "Linkers and Cleavage Strategies in Solid-Phase Organic Synthesis and Combinatorial Chemistry", *Chem. Rev.*, 100:2091-2157, 2000.

Usman et al., "Automated chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecules of an *Escherichia coli* Formylmethionine tRNA", *J. Am. Chem. Soc.*, 109:7845-7854, 1987.

Damha and Ogilvie, "Synthesis and Spectroscopic Analysis of Branched RNA Fragments: Messenger RNA Splicing Intermediates", *J. Org. Chem.*, 53:3710-3722, 1988.

Hadden et al., "Constant time inverse-detection gradient accordion resealed heteronuclear multiple bond correlation spectroscopy: CIGAR-HMBC", *Magnetic Resonance in Chemistry*, 38:143-147, 2000.

Backes et al., "Acitvation method to Prepare a Highly Reactive Acylsulfonaminde 'Safety-Catch' Linker for Solid-Phase Synthesis", *J. Am. Chem. Soc.*, 118:3055-3056, 1996.

Davis, "Task-Specific Ionic Liquids", *Chemistry Letters*, 33(9):1072-1077, 2004.

Huo and Chan, "A novel liquid-phase strategy for organic synthesis using organic ions as soluble supports", *Chemical Society Reviews*, 39:2977-3006, 2010.

\* cited by examiner

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Leu Phe Gly Gly
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Leu Phe Gly Gly Tyr
1               5
```

IONIC LIQUID SUPPORTED SYNTHESIS

CROSS REFERENCE TO RELATED APPLICATIONS

The present application is a national phase application under 35 U.S.C. § 371 of International Application No. PCT/CA2006/000355 filed 15 Mar. 2006, which claims the benefit of U.S. Provisional Application No. 60/661,480 filed 15 Mar. 2005. The entire contents of these applications are incorporated by reference.

FIELD OF THE INVENTION

The present invention relates to ionic liquid supported synthesis. More specifically, the present invention relates to ionic liquid supported oligopeptide, oligosaccharide and oligonucleotide synthesis. Yet more specifically, the present invention relates to ionic liquid supported synthesis of bioactive oligopeptides.

BACKGROUND OF THE INVENTION

The efficient synthesis of oligopeptides, oligosaccharides and oligonucleotides represents a contemporary challenge which has led to the development of several novel approaches. The traditional access to structurally defined oligosaccharides using solution-phase synthesis is laborious and requires purification of the reaction products by chromatography after each step.[1]

The demand of the scientific community for synthetic oligonucleotides has grown exponentially over the past decades. Fortunately, the abundant source of DNA oligonucleotide primers has satisfied the tremendous needs of the genome sequencing efforts, functional genomics, and polymerase chain reaction (PCR)-based detection methods. Moreover, oligonucleotides have widespread use in the development of therapeutics and diagnostic applications, including chip-based DNA microarrays. Significant advances in structural biology and biochemistry have been achieved through concomitant advances in DNA and RNA chemistry.[2-6] For instance, the current state of the art in ribozyme and siRNA research, including crystal structures, would not have been possible without the accompanying improvements in RNA synthesis.[4]

Since Merrifield[7] and Letsinger et al.[8,9] introduced the use of polymer supports for the synthesis of oligopeptides and oligonucleotides respectively, the use of insoluble supports has become an important tool for organic synthesis, especially in the synthesis of biopolymers such as oligonucleotides, peptides and more recently, carbohydrates.[10-12] The facile purification process comprising removing excess reagents and side products by filtration allows for straightforward product isolation and makes automation possible. Although extremely successful, because of the heterogeneous nature of the insoluble polymers, solid phase synthesis retains drawbacks that are typically associated with heterogeneous reaction conditions in addition to the high cost of the solid supports themselves, making large scale synthesis of these compounds very expensive.

Recent advances in polymer-supported solid-phase synthesis[13-15] has provided an easier way to assemble complex oligosaccharides because it allows for removal of the excess reagents by simply washing the resins and thus minimizes the number of chromatographic steps required.[16,17] This has led to impressive examples of successful automated synthesis.[14,18] However, the disadvantages of solid-phase synthesis are that large excess of the expensive carbohydrate unit is often required to drive the heterogeneous reaction to completion and it is more difficult to monitor the sugar-sugar coupling process by normal characterization methods such as TLC, NMR and mass spectrometry. Moreover, despite the many benefits offered by the solid phase approach, the heterogeneous nature of the insoluble polymers and reaction conditions often results in a series of problems including non-linear reaction kinetics, unequal distribution of and/or access to the reaction sites, solvation problems and inefficient coupling rate.

The search for alternative methodologies, with the aim of restoring homogeneous reaction conditions and overcoming some of the disadvantages of solid phase synthesis, has led to the development of soluble polymer supports. In recent years, the use of soluble polymer supports has received considerable attention because such "liquid phase" synthesis retains much of the advantages of conventional solution chemistry, while still allowing the advantage of facilitated purification of the product. Soluble polyethylene glycol (PEG), polyvinyl alcohol and other polymers have all been successfully employed for the synthesis of oligopeptides[19] and nucleotides.[11] Moreover, soluble polyethylene glycol (PEG) polymers have also been used as supports for oligosaccharide[12,20-23] and small molecule synthesis.[24] However, the use of soluble polymer supports suffer from the drawback of low loading capacity, difficulties in the selective precipitation of the oligosaccharide-attached polymer, limited solubility during the synthesis of longer peptides, low aqueous solubility, lack of solubility in ether solvents[24] and energy intensive cooling required for purification.

More recently, a new solution-phase synthesis based on fluorinated (fluorous) soluble supports has been advocated.[25] The approach is based on the preferential solubility of the fluorous support and the fluorinated reagents in fluorous solvents (i.e. perfluoroalkanes). The non-fluorinated reagents can be readily separated from the supported product through fluorous-organic solvent partitioning[26a-d] or fluorous silica gel-based solid-phase extraction (SPE).[26e-h] This approach requires the use of fluorinated compounds which are not generally readily available. Purification can be achieved through a temperature switch that causes a phase separation between the previously miscible fluorous solvent and the organic solvent, thus facilitating separation. The use of fluorous phase methodology for organic synthesis has been demonstrated for the synthesis of oligopeptides[27], oligosaccharides[28] and small molecules.[25] In the case of oligosaccharide synthesis it has been demonstrated that the solubility of the saccharide-anchored support in the fluorous solvent depends on the fluorine content[28b] which declines as the number of saccharide units increases. The expense of perfluoroalkane solvents, the need for specialized fluorinated reagents and the energy cost associated with the temperature switch are potential limitations prohibiting a broad application of fluorous phase organic synthesis.

Ionic liquids (ILs) have received much attention in recent years as environmentally benign reaction media for organic reactions.[29] A practical definition of an ionic liquid is that it is a salt with melting temperature below, often much below, the boiling point of water. A common feature of ionic liquids is that most have organic cations and inorganic anions. Non-limiting examples of ionic liquids are the alkylimidazolium and pyridinium salts of halides, tetrafluoroborate and hexafluorophosphate. Numerous chemical reactions, including some enzymatic reactions, can be carried out in ionic liquids.[30] Room temperature ionic liquids have also been widely explored as media for electrochemical technologies,

[31] chemical extractions[32], and other industrial processes.[33] This is due to some intriguing chemical and physical properties of ionic liquids: high thermal and chemical stability, non-flammability, lack of measurable vapor pressure and high loading capacity. In most cases, ionic liquids can be readily recycled. By modifying the structure of the cation or the anion, the solubilities of the ionic liquids can be readily tuned so that they can phase separate from organic as well as aqueous media, thus facilitating separation and purification. This offers the potential that ionic liquids can serve as viable soluble functional supports for organic synthesis. The substrate solubility can also be tuned.[34] Recent reports have successfully demonstrated the efficiency of ILSS (Ionic Liquid Supported Synthesis) for small molecules[35,37,38] and small peptides.[39] The possibility of developing recoverable and recyclable ionic liquid supported catalysts have also been explored.[36]

The use of an ionic liquid as a matrix (i.e. solvent) for organic reactions has been previously described by Vaultier et al. (WO 2004/029004). The organic reactions are carried out using functionalized salts known as "onium salts" which serve as soluble supports. The ionic liquid assures the solubilization of the functionalized salts such that the reactions can be carried out under homogeneous conditions. Vaultier et al. (WO 2005/005345) have also previously described the use of onium salts (i.e. ionic liquids) dissolved in at least one organic solvent, coined "Onium Salt Supported Organic Synthesis", as soluble supports for organic reactions.

There thus remains a need for improved methods for the synthesis of oligomers, including but not limited to oligopeptides, oligosaccharides, and oligonucleotides which methods combine the advantages of both solid-phase and solution phase synthesis, which method comprises homogeneous solution-phase conditions and which method allows for the ready purification of the product.

The present invention seeks to meet these and other needs.

The present description refers to a number of documents, the content of which is herein incorporated by reference in their entirety.

SUMMARY OF THE INVENTION

The present invention relates to ionic liquid (i.e. ionic liquid) supported synthesis.

In an embodiment, the present invention relates to the synthesis of oligopeptides, oligosaccharides and oligonucleotides, supported by ionic liquids.

In an embodiment, the present invention relates to ionic liquid supported methods for the synthesis of oligomers, including but not limited to oligopeptides, oligosaccharides and oligonucleotides.

In an embodiment, the present invention relates to a method of synthesizing oligomers selected from the group consisting of oligopeptides, oligosaccharides and oligonucleotides, the method comprising contacting a first monomer unit with an ionic liquid at reaction conditions to provide an ionic liquid bound monomer unit; and contacting the ionic liquid bound monomer unit with at least one further monomer unit at reaction conditions to provide an ionic liquid bound oligomer comprising from 2 to 30 monomer units. The ionic liquid bound oligomer is then cleaved from the ionic liquid to provide the liberated oligomer.

In a further embodiment, the present invention relates to a method for synthesizing oligomers selected from the group consisting of oligopeptides, oligosaccharides and oligonucleotides, the method comprising so employing an ionic liquid to monomer units as to result in oligomers comprising from 2 to 30 monomer units.

In a further embodiment, the present invention relates to ionic liquids for use in chemical synthesis and capable of serving the dual function of both solvent and liquid support. In a particular embodiment the ionic liquid is an organic salt comprising a heterocyclic or substituted heterocyclic quaternary nitrogen-containing organic cation, a heterocyclic or substituted heterocyclic quaternary phosphonium containing organic cation, or a heterocyclic or substituted heterocyclic trivalent sulfonium containing organic cation; and an anion balancing the charge on the organic cation. In a more particular embodiment the organic cation is selected from the group consisting of N-substituted pyridine and 1,3-disubstituted imidazole. The anion balancing the charge on the organic cation may be selected from the group consisting of $Cl^-$, $Br^-$, $BF_4^-$, $PF_6^-$, $SbF_6^-$, $CuCl_2^-$, and $AlCl_4^-$. Other suitable anions could also be used and are well within the capacity of a skilled technician.

In a particular embodiment, the present invention relates to the ionic liquid supported synthesis of oligopeptides. In yet a more particular embodiment, the present invention relates to the synthesis of pentapeptide Leu[5]-enkephalin, the structure of which is shown below.

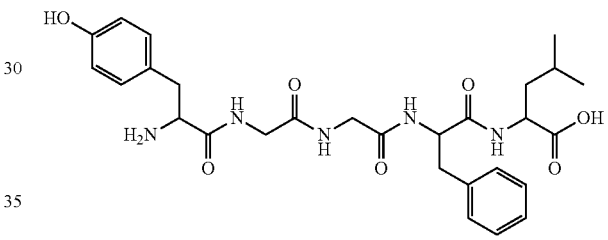

Leu-enkephalin

The foregoing and other objects, advantages and features of the present invention will become more apparent upon reading of the following non restrictive description of illustrative embodiments thereof, given by way of example only with reference to the accompanying drawings.

DETAILED DESCRIPTION OF ILLUSTRATIVE EMBODIMENTS

Figure 1:
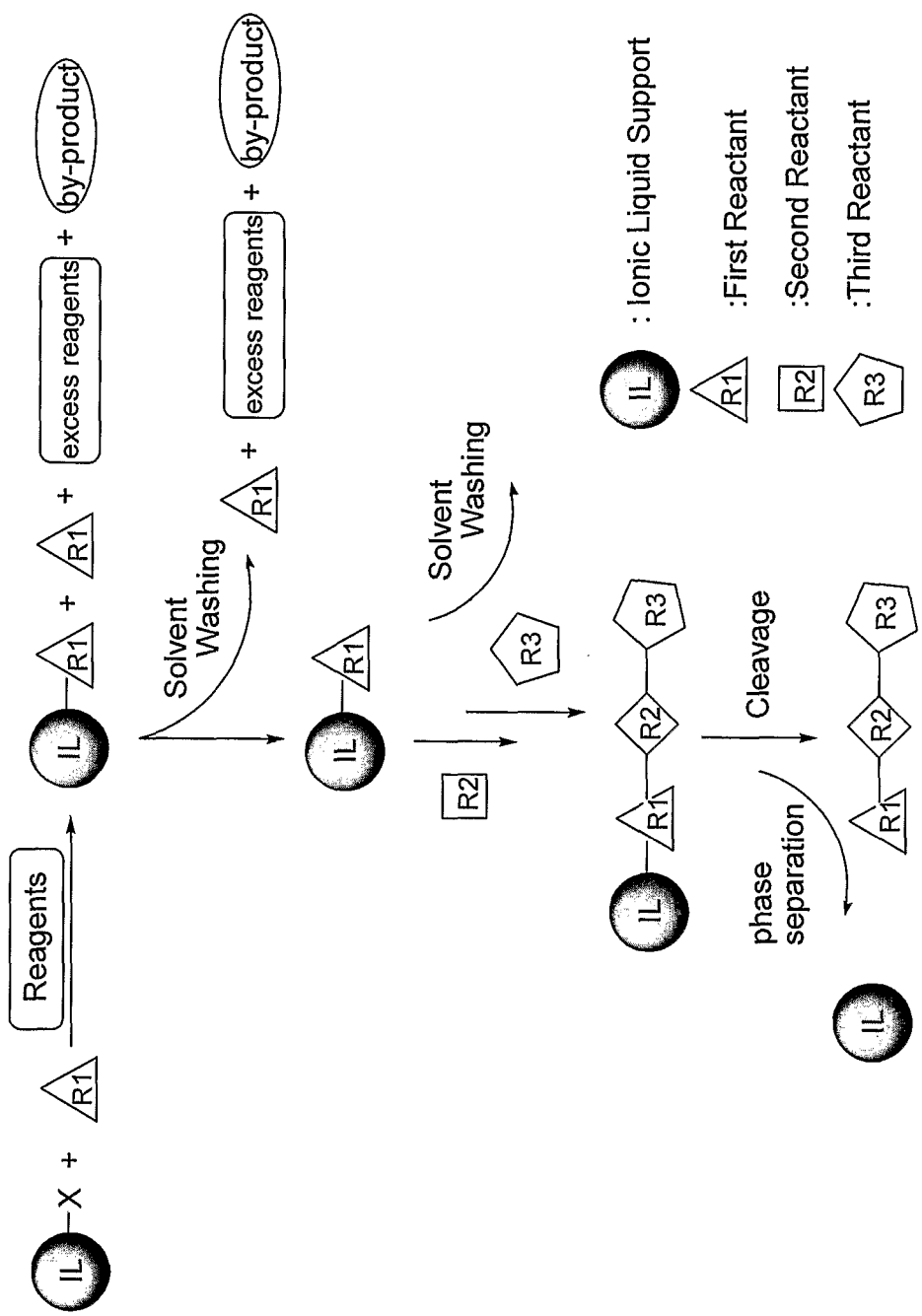
FIG. 1 is an illustration of an embodiment of the general concept of ionic liquid supported synthesis in accordance with the present invention.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with a or more substituents including but not limited to alkoxy, halogen and nitro groups). Beta and gamma amino acids are also within the scope of the term "amino acid". Amino acids protected by standard protecting groups commonly used in peptide synthesis are also within the scope of the term "amino acid". These compounds are known to persons skilled in the art of peptide chemistry.

The term "nucleotide" as used herein is understood as referring to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification selected from (a) an alternative linking group, (b) an analogous form of purine, (c) an analogous form of pyrimidine, or (d) an analogous sugar. Nucleotides protected by standard protecting groups commonly used in oligonucleotide synthesis are also within the scope of the term "nucleotide". These compounds are known to persons skilled in the art of nucleotide chemistry.

The term "saccharide", as used herein, is understood as referring to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Monosaccharides include, but are not limited to, ribose, 2-deoxy-ribose, glucose, mannose, xylose, galactose, fucose, fructose, etc. Disaccharides contain two monosaccharide units joined by a glycosidic linkage. Disaccharides include, for example, sucrose, lactose, maltose, cellobiose, and the like. Oligosaccharides typically contain from 2 to 10 monosaccharide units joined in glycosidic linkage. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc. A saccharide may also reside as a component part of a larger molecule, for example, as the saccharide moiety of a nucleoside, a nucleotide, a polynucleotide, a DNA, an RNA, etc. The term "saccharide", as used herein, is also understood as encompassing modified saccharides such as those comprising at least one modification selected from (a) replacement of one or more of the OH groups by substituents including but not limited to H, $NH_2$, halogen, alkyl, aryl; (b) oxidation of one or more of the OH groups into functional groups including aldehydes, ketones, acids, esters, and derivatives thereof. Saccharides protected by standard protecting groups commonly used in oligosaccharide synthesis are also within the scope of the term "saccharide". These compounds are known to persons skilled in the art of peptide chemistry.

The terms "growing oligopeptide chain", "growing oligosaccharide chain" and "growing oligonucleotide chain" as used herein refers to a chain that has been prepared by the sequential addition of amino acids, saccharides or nucleotides, optionally suitably protected. After each reaction cycle the growing oligopeptide, oligosaccharide or oligonucleotide increases in length by at least one amino acid, saccharide or nucleotide, and becomes the starting material for the next reaction cycle. As used herein the term can refer to either starting material or product and one of ordinary skill in the art will recognize what is intended by the term in a particular context.

The term "alkyl group" as used herein is understood as referring to a saturated, monovalent unbranched or branched hydrocarbon chain. Examples of alkyl groups include, but are not limited to, $(C_1-C_6)$-alkyl groups. Examples of $(C_1-C_6)$-alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "aryl" as used herein is understood as referring to 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions. Aryl groups can also be part of a polycyclic group. For example, aryl groups include fused aromatic moieties such as naphthyl, anthracenyl, quinolyl, indolyl, and the like.

The term "halogen" as used herein is understood as referring to fluorine, chlorine, bromine, or iodine. Correspondingly, the meaning of the term "halo" is understood to encompass fluoro, chloro, bromo, and iodo.

Protecting groups in the present invention are used in conjunction with oligopeptide syntheses, oligonucleotide syntheses and oligosaccharide syntheses. The protecting groups block a reactive end of the monomer, whether an amino acid, a saccharide, or a nucleotide. The nature of the chemical synthesis will dictate which reactive group will require a protecting group. Regardless of the specific use, protecting groups are employed to protect a moiety on a molecule from reacting with another reagent. Protecting groups as used in the present invention have the following characteristics: they prevent selected reagents from modifying the group to which they are attached; they are stable (that is, they remain attached to the molecule) to the synthesis reaction conditions; and they are removable under conditions that do not adversely affect the remaining structure. The selection of a suitable protecting group will depend, of course, on the chemical nature of the monomer unit and oligomer, as well as the specific reagents they are to protect against. It is well within the capacity of a skilled technician to select a suitable protecting group for a given reaction sequence.

The present description refers to a number of chemical terms and abbreviations used by those skilled in the art. Nevertheless, definitions of selected terms are provided for clarity and consistency.

Abbreviations: DCC: Dicyclohexylcarbodiimide; DMAP: 4-(N,N-dimethylamino)pyridine; EDC: 1-(3-dimethylaminopropyl)-3-ethylcarbodiimide hydrochloride; HOBt: 1-hydroxybenzotriazole hydrate; HATU: O-(7-azabenzotriazol-1-yl)-N,N,N',N'-tetramethyluronium hexafluorophosphate; PyBOP: (benzotriazol-1-yloxy)tripyrrolidinophosphonium hexafluorophosphate; DCU: dicyclohexylurea; DIPEA (Hunig's base): diisopropylethylamine; DCI: 4,5-dicyanoimidazole; DMSO: dimethylsulfoxide; DMSO-d6: deuterated dimethylsulfoxide; DCM: dichloromethane; NMI: N-methylimidazole; TEA: triethylamine; TEAA: triethylammonium acetate; THF: tetrahydrofuran; CE: cyanoethyl; PEG: polyethylene glycol; Py: pyridine; Succ: succinyl; CPG: controlled-pore glass; IL: ionic liquid; ILSS: ionic liquid supported synthesis; DMT: dimethoxytrityl; LCAA: long chain alkyl amine; EEDQ: 2-ethoxy-1-ethoxycarbonyl-1,2-dihydroquinoline; IIDQ: 2-isobutoxy-1-isobutoxycarbonyl-1,2-dihycroquinoline; TFA: Trifluoroacetic acid; AcOH: acetic acid; NMR: Nuclear Magnetic Resonance; MS: Mass Spectrometry; m/z: mass to charge ratio; m.p.: melting point; FAB: Fast Atom Bombardment; TLC: Thin Layer Chromatography; ESI: electrospray ionization; FTMS: Fourier Transform Mass Spectrometer; LCMS: liquid chromatography-mass spectrometry; J; coupling constant; s: singlet; t: triplet; m: multiplet; P-III: trivalent phosphorus; P-V: pentavalent phosphorus.

Figure 2:
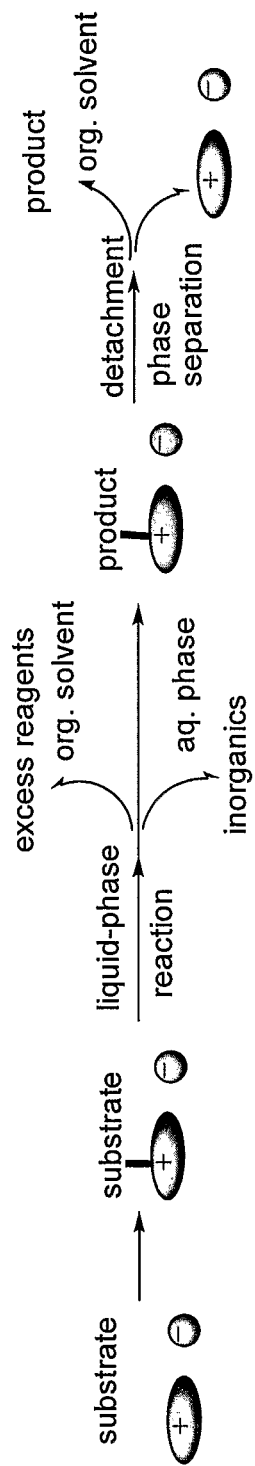
FIG. 2 is an illustration of a further embodiment of the general concept of ionic liquid supported synthesis in accordance with the present invention.

The general concept of ionic liquid supported synthesis in accordance with the present invention is illustrated in FIGS. 1 and 2. The substrate (reactant) anchored onto an ionic liquid moiety is soluble in polar organic solvents and can undergo liquid-phase reaction. After completion of the reaction and evaporation of the solvent, the excess reagents can be removed by a less polar organic solvent in which the ionic liquid-anchored product is not soluble. Inorganic reagents and/or side products can be removed by precipitation or by washing with aqueous solution. The sequence of reactions can be repeated to give more complex structures. Finally, the product can be detached and then separated from the ionic liquid moiety by organic solvent extraction. The substrates anchored to the ionic liquid support are expected to largely retain their reactivity analogously to traditional solution based reactions. The progress of the reactions carried out on ionic liquid supports are readily monitored and analyzed by standard spectroscopic techniques.

A novel solution phase approach to the synthesis of oligopeptides, oligosaccharides and oligonucleotides, supported by ionic liquids, is described herein.

In an embodiment, the present invention relates to ionic liquid supported methods for the synthesis of oligomers, including but not limited to oligopeptides, oligosaccharides and oligonucleotides. In a further embodiment, the present invention relates to ionic liquids for use in chemical synthesis of oligomers, including but not limited to oligopeptides, oligosaccharides and oligonucleotides, the ionic liquids being capable of serving the dual function of both solvent and liquid support. The ionic liquids are compatible with the various synthetic methodologies generally applied in organic synthesis. More specifically, the ionic liquids are compatible with the various synthetic methodologies generally applied in the synthesis of oligomers, including but not limited to oligopeptides, oligosaccharides and oligonucleotides. Furthermore, particularly but not exclusively in the case of oligopeptide synthesis, the ionic liquids, due to their inherent ionic nature, must not induce racemization or epimerization of the peptide building blocks. Moreover, the solubility of the ionic liquid supports must not be influenced by the growing oligopeptide, oligosaccharide or oligonucleotide chain, such that separation and purification procedures become unduly complex. Separation and purification procedures are greatly simplified and generally involve washing steps with aqueous and organic solvents.

In an embodiment of the present invention, the ionic liquid is an organic salt comprising a heterocyclic or substituted heterocyclic quaternary nitrogen-containing organic cation and an anion balancing the charge on the organic cation. In a particular embodiment the organic cation is selected from the group consisting of N-substituted pyridine and 1,3-disubstituted imidazole and the anion is selected from the group consisting of $Cl^-$, $Br^-$, $BF_4^-$, $PF_6^-$, $SbF_6^-$, $CuCl_2^-$, and $AlCl_4^-$. Other ionic liquids are known in the art, and are within the capacity of a skilled technician. Furthermore, it is within the capacity of a skilled technician that the anion may also be an organic anion, non-limiting examples of which include $CH_3CO_2^-$, $CF_3CO_2^-$, $CH_3SO_4^-$, and $CF_3SO_2^-$.

The present invention is illustrated in further detail by the following non restrictive description of illustrative embodiments.

EXAMPLE 1

Attachment to Ionic Liquid Support and Test for Racemization (Scheme 1)

3-Hydroxyethyl-(1-methylimidazolium )-tetrafluoroborate (1), readily available from the reaction of 1-methylimidazole and 2-bromoethanol[35a,d] was chosen as a non-limiting example of a suitable ionic liquid support to illustrate the ionic liquid supported oligopeptide synthesis as contemplated by the present invention. Other ionic liquid supports capable of being used in accordance with the present invention are known in the art and are within the capacity of a skilled technician.

Scheme 1

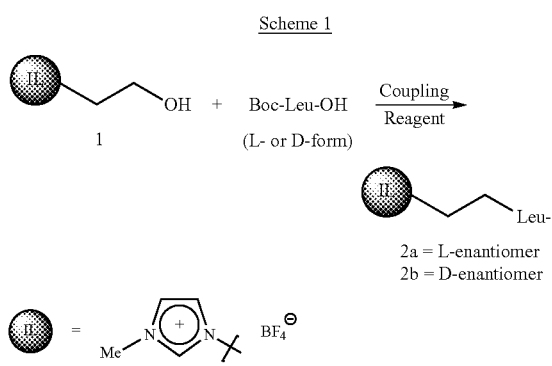

2a = L-enantiomer
2b = D-enantiomer

Various coupling reaction conditions were examined for the loading of the first amino acid, Boc-leucine, on to 1. The efficacy of these coupling reactions is shown below in Table 1.

TABLE 1

Loading of the first amino acid (Boc-Leu-OH) onto ionic liquid support 1.

| Entry | Coupling Reagent[a] | Condition | Conversion (%)[b] |
|---|---|---|---|
| 1 | EDC (2 eq.)/HOBt | CH$_3$CN/rt/48 h | 45 |
| 2 | HATU (2 eq.)/HOBt | CH$_3$CN/rt/48 h | 53 |
| 3 | PyBOP (2 eq.)/DIPEA | CH$_3$CN/rt/48 h | 55 |
| 4 | EEDQ (1.5 eq.) | CH$_3$CN/35° C./18 h | 71 |
| 5 | EEDQ (1.5 eq.) | CH$_3$CN/35° C./72 h | 77 |
| 6 | EEDQ (5 eq.) | CH$_3$CN/60° C./18 h | 86 |
| 7 | IIDQ (2 eq.) | CH$_3$CN/35° C./48 h | 87 |
| 8 | DCC (2 eq.)/DMAP | CH$_3$CN/rt/48 h | 100 |

[a]Equivalent of the coupling reagent to Boc-Leu-OH;
[b]Determined by $^1$H NMR analysis.

Among the coupling conditions explored, the DCC/DMAP combination (entry 8) provided the best results. Other explored coupling conditions include the combinations EDC/HOBt; HATU/HOBt; PyBOP/DIPEA, EEDQ or IIDQ. However, the latter conditions were not sufficient to push the coupling reaction (i.e. esterification reaction) to quantitative conversion. An alternative and useful coupling route to the DCC/DMAP route, even though involving an additional capping step, comprises capping of unreacted 1 with acetic anhydride. By sequential ether and aqueous acid washings, excess Boc-leucine, DMAP and the DCU by-product were all removed. The ionic liquid supported Boc-leucine 2 was obtained in high isolated yield (91%) and good purity as verified by NMR spectroscopy. The coupling reaction was carried out using both L- and the D-Leu-Boc to give 2a and 2b respectively.

Various Boc-deprotection reaction conditions of 2a and 2b were examined, the results of which are shown below in Table 2. Both tetrafluoroboric acid and trifluoroacetic acid could induce very clean deprotection as indicated by $^1$H NMR spectroscopy. Even though not as efficient, Boc deprotection could also performed using acidic ion exchange resins such as Dowex™ 50W×8–100 or Amberlyst™ 15. Other deprotection methods such as described in "Protective Groups in Organic Synthesis" (Greene et al., John Wiley & Sons, Inc., NY, 1991) are capable of being used in accordance with the present invention and are within the capacity of a skilled technician.

TABLE 2

Deprotection and coupling of ionic liquid supported Leu-Boc 2a and 2b with Boc-Phe-OH

| Entry | Deprotection/ Neutralization | Coupling Conditions[a] | Conversion (%)[b] |
|---|---|---|---|
| 1 | TFA/no neutralization | EEDQ (2.5 eq.)/CH$_3$CN/ 35° C./48 h | 55 |
| 2 | TFA/no neutralization | DCC (2 eq.)/DMAP/CH$_3$CN/ rt/48 h | 60 |
| 3 | TFA/NaHCO$_3$ | EEDQ (2.5 eq.)/CH$_3$CN/ 35° C./48 h | 60 |
| 4 | TFA/Et$_3$N | IIDQ (2 eq.)/CH$_3$CN/ 35° C./48 h | 85 |
| 5 | TFA/NaHCO$_3$ | DCC (2 eq.)/DMAP/CH$_3$CN/ rt/48 h | 85 |
| 6 | TFA/Et$_3$N | DCC (2 eq.)/DMAP/CH$_3$CN/ rt/48 h | 95 |
| 7 | TFA/DIPEA | PyBOP (1.5 eq.)/DIPEA (3 eq.)/CH$_3$CN/35° C./30 h | 100 |
| 8 | HBF$_4$/OH$^-$ resin | EEDQ (2.5 eq.)/CH$_3$CN/ 35° C./48 h | 25 |
| 9 | HBF$_4$/NaHCO$_3$ | EEDQ (2.5 eq.)/CH$_3$CN/ 35° C./48 h | 60 |

[a]Equivalent of the coupling reagent to Boc-Phe-OH;
[b]Determined by $^1$H NMR analysis.

Coupling of the next amino acid building block, i.e. Boc-Phe-OH (Scheme 2), is preferably preceded by a neutralization step (Table 2). Any excess TFA or HBF$_4$, previously used in the Boc-deprotection, may be neutralized with NaHCO$_3$, Et$_3$N, DIPEA, or a basic ion exchange resin like Dowex™ 550A OH. Other suitable neutralizing agents capable of being used in accordance with the present invention are known in the art and are within the capacity of a skilled technician. Surprisingly, when the coupling reaction of the next amino acid building block, i.e. Boc-Phe-OH, is carried out using the PyBOP/DIPEA conditions, both the deprotection/neutralization and the subsequent coupling reaction can be carried in sequence without any intermediate separation and purification and steps.

Scheme 2

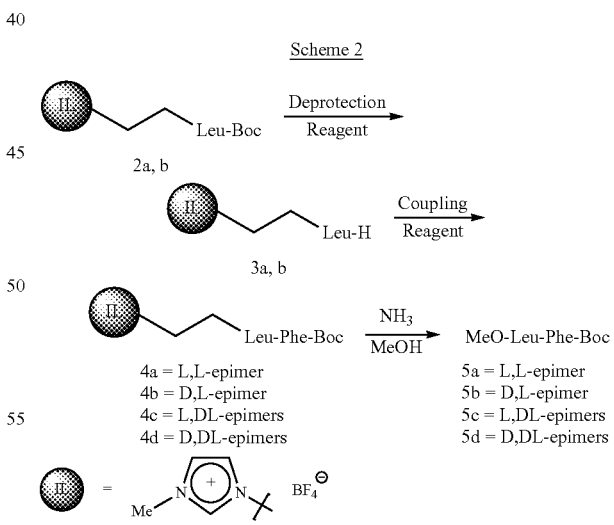

4a = L,L-epimer        5a = L,L-epimer
4b = D,L-epimer        5b = D,L-epimer
4c = L,DL-epimers      5c = L,DL-epimers
4d = D,DL-epimers      5d = D,DL-epimers Peptide 4a was obtained in essentially quantitative yield.[40] An advantage of the ionic liquid supported methods of the present invention is that a large excess of reagents is not required. The coupling reactions could be achieved with only 1.2 eq. of PyBOP and Boc-Phe-OH.

In order to assess the potential for racemization or epimerization during ionic liquid supported synthesis, more specifically during the loading step using DCC/DMAP conditions, a series of ionic liquid supported dipeptides 4a-d were synthesized. The peptides were subsequently cleaved using ammonia/methanol to provide dipeptides 5a-d. Subsequent HPLC analysis of 5a (L,L) and 5b (D,L) revealed no detectable amounts of other isomers (<0.5%), indicating that during the loading step and subsequent dipeptide synthesis, no significant racemization or epimerization occurred. Moreover, the results also suggest the absence of racemization or epimerization during the cleavage step using basic conditions (ammonia/methanol).

EXAMPLE 2

Oligopeptide Synthesis and Detachment from the Ionic Liquid Support

Two successive glycine moieties, followed by a tyrosine moiety (all in their protected Boc form), were next coupled to the growing peptide chain 4a utilizing the previously developed coupling and deprotection conditions to provide the ionic liquid supported pentapeptide 11 as a foam-like pale yellow solid (Scheme 3). During the synthetic sequence, all the intermediates, either in Boc-protected form (7, 9, 11) or in deprotected form (6, 8, 10) were isolated and purified by standard protocols well known to a person skilled in the art. Such protocols generally involve sequential organic solvent(s) and aqueous washings, non-limiting examples of which are described herein.

oligopeptides (2a, 4a, 7, 9 and 11) further aided structural characterization; the most intense signal corresponding to the cation of the ionic liquid supported oligopeptide.

Two routes for liberating the pentapeptide product, Leu[5]-enkaphalin 14, from the ionic liquid support were evaluated (Scheme 3). A first route involved cleaving the pentapeptide 14 from the ionic liquid support under basic aqueous conditions, followed by removing the Boc and t-Bu-protecting groups using TFA/anisole. A second route involved first removing the Boc and t-Bu-protecting groups using TFA/anisole, followed by cleaving the pentapeptide 14 from the ionic liquid support under basic aqueous conditions. The first route provides for the protected pentapeptide 12 to precipitate out of the solution in good yield and purity (84% yield) following cleavage from the ionic liquid support and acidification of the reaction medium.

Figure 3:
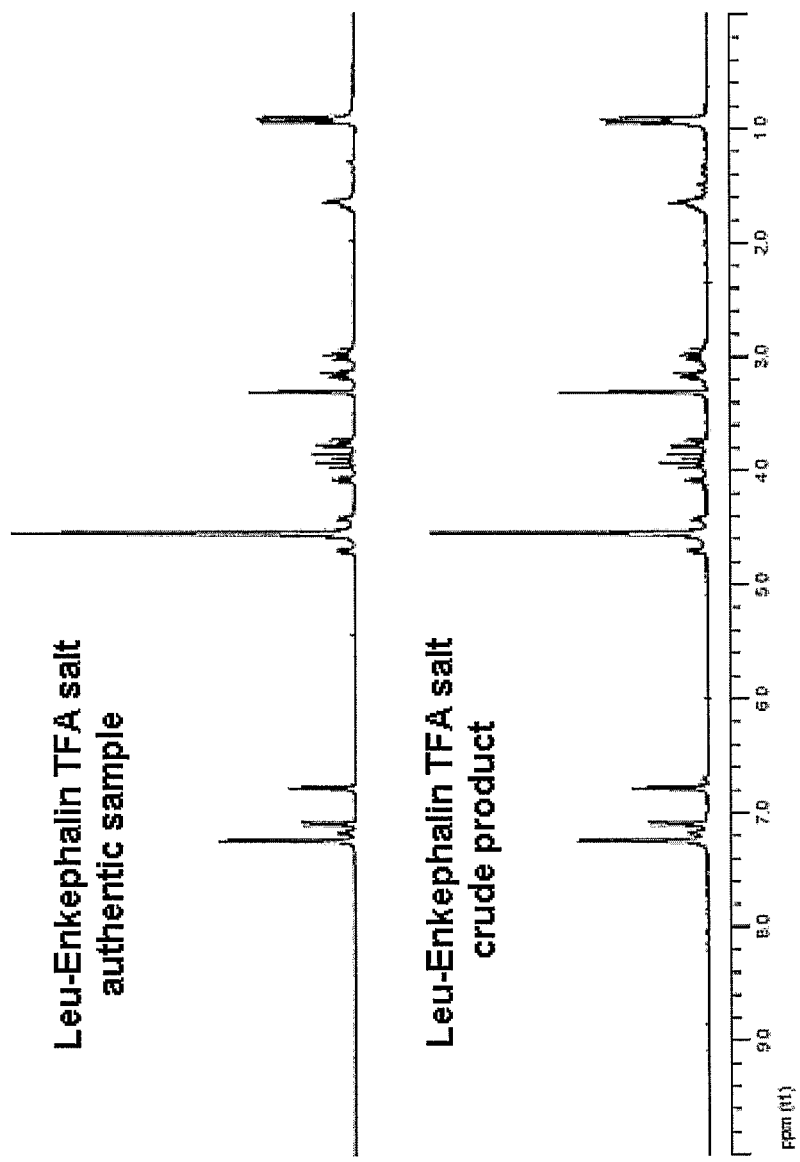
FIG. 3 is an illustration of the $^1$H NMR spectrum of a TFA salt of authentic Leu[5]-enkephalin[41] and synthetic Leu[5]-enkephalin 14.
Figure 4:
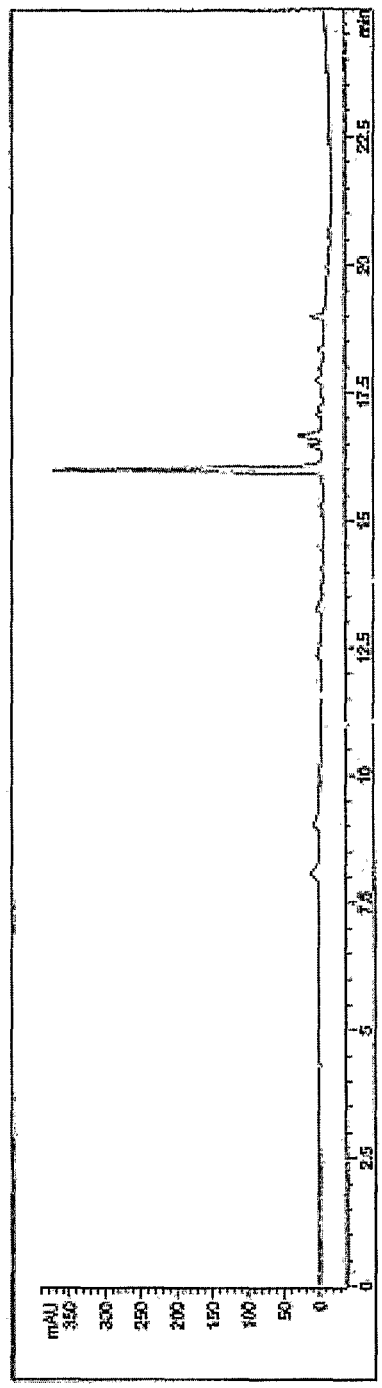
FIG. 4 is an illustration of the HPLC analysis of crude Leu[5]-enkephalin 14 as synthesized by ILSS;[42]
Figure 5:
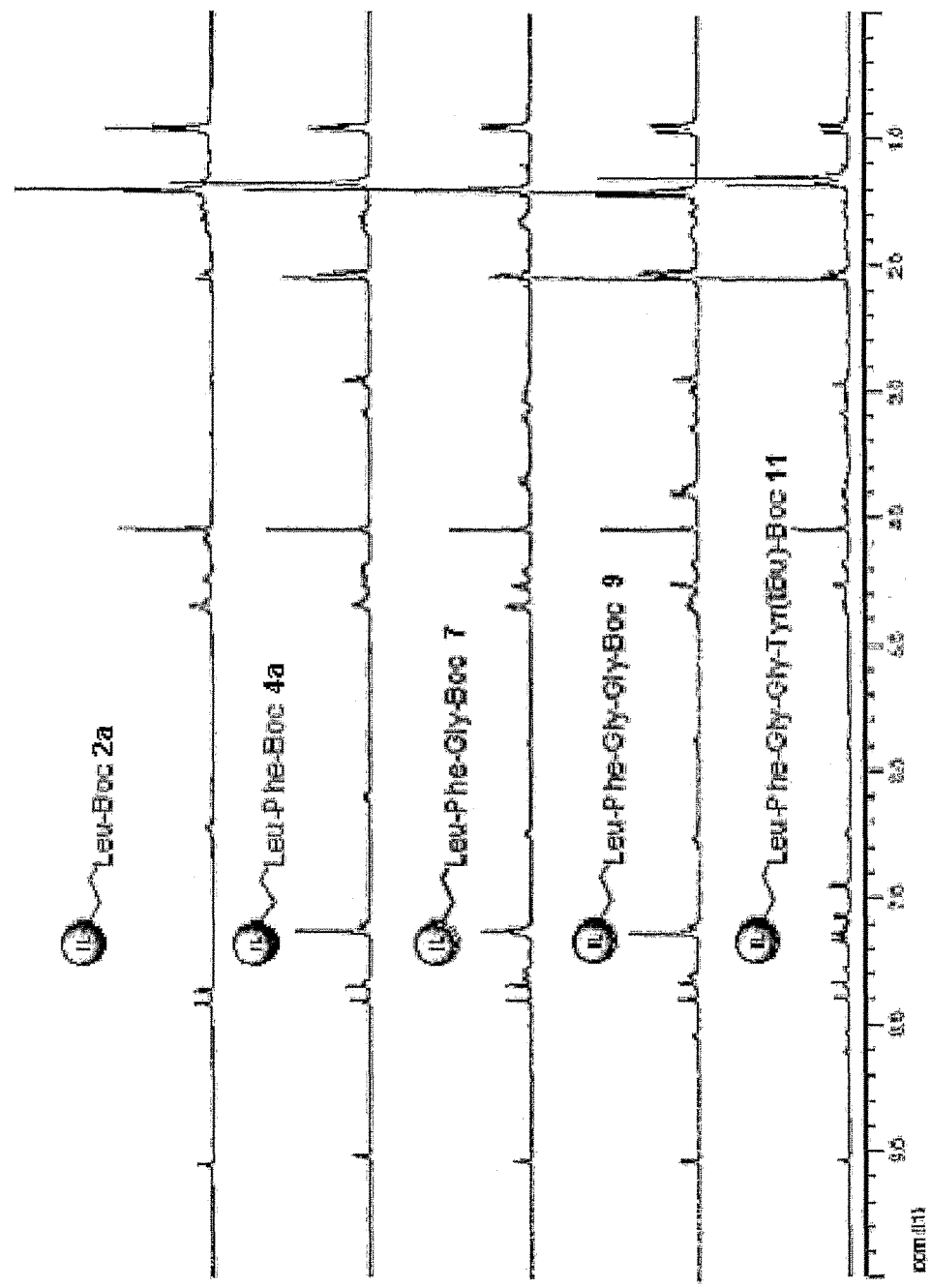
FIG. 5 is an illustration of the $^1$H NMR spectra of ionic liquid supported peptides 2a, 4a, 7, 9 and 11.
Figure 6:
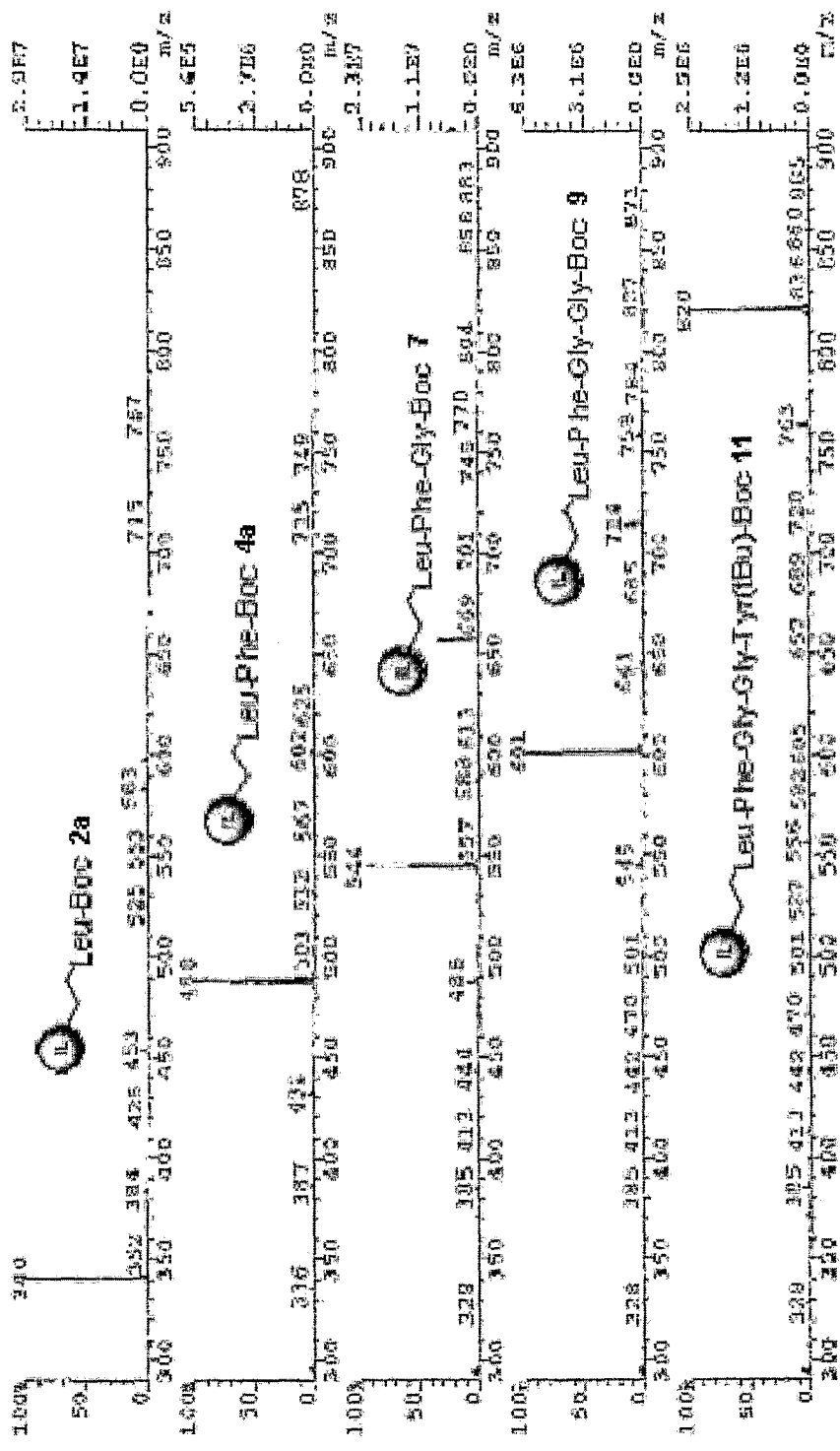
FIG. 6 is an illustration of the mass spectra of ionic liquid supported peptides 2a, 4a, 7, 9 and 11.

The purity of the Leu[5]-enkephalin pentapeptide 14 thus prepared was analyzed. The pentapeptide 14 was obtained in 50% overall yield from 1 without any recrystallization or chromatography procedure as its corresponding TFA salt [m.p. 148-152° C. and $[\alpha]^{20}_D$=−25.0 (c: 0.8, 95% AcOH)]. An authentic sample of 14 has a melting point range of 150-153° C. and an specific rotation $[\alpha]^{20}_D$=−25.6 (c: 0.9, 95% AcOH)].[41] The $^1$H NMR spectrum of 14 was essentially identical to that obtained with an authentic sample (FIG. 3). The purity of the Leu[5]-enkephalin pentapeptide 14 was determined to be in excess of about 90% pure, as demonstrated by HPLC analysis (FIG. 4). This level of purity is

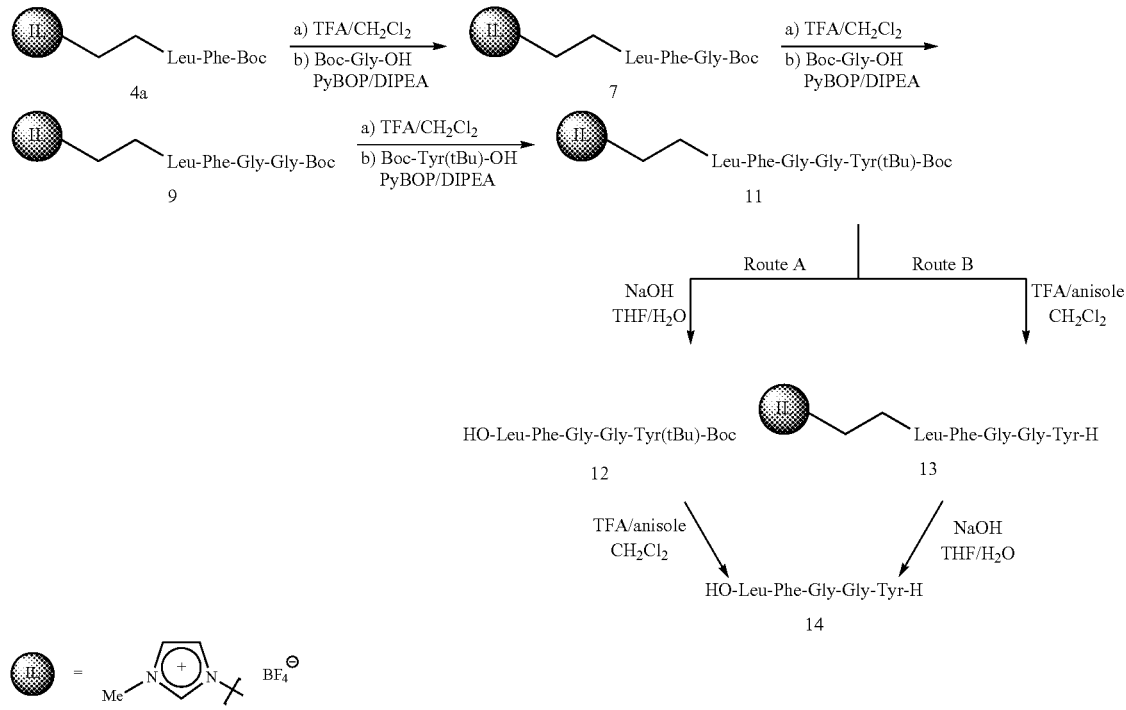

Scheme 3

Structural confirmation and purity analyses were realized by conventional spectroscopic methods such as $^1$H, $^{13}$C NMR and MS. The presence or absence of the t-butyl protons of the Boc group in the $^1$H NMR spectrum was characteristic of the coupling or the deprotection step respectively. The mass spectra of the ionic liquid supported superior to what is generally obtained by solid phase peptide synthesis prior to chromatography purification.[42]

The ionic liquid supported synthesis, as embodied by the synthesis of the Leu[5]-enkephalin pentapeptide 14, offers some potential advantages over many of the existing methods of peptide synthesis (Table 3).

TABLE 3

Comparison of conventional and various supported peptide synthesis methods.[a]

| Aspect | CSPPS | SPPS | SPSPS | FPPS | ILSPS |
|---|---|---|---|---|---|
| Generic protocol | − | + | + | + | + |
| Homogeneous synthesis | + | − | + | + | + |
| High loading capacity | n/a | − | − | + | + |
| Low excess reagents | + | − | + | + | + |
| Facile purification | − | + | + | + | + |
| Routine spectroscopic analysis | + | − | +/− | + | + |
| Relatively low cost | +/− | − | − | − | + |

[a]CSPPS: Conventional solution phase peptide synthesis; SPPS: Solid phase peptide synthesis; SPSPS: Soluble polymer supported peptide synthesis; FPPS: Fluorous phase peptide synthesis; ILSPS: Ionic liquid supported peptide synthesis.

Firstly, in common with other solution phase methodologies, the use of a large excess of reaction reagents can be avoided in contrast to solid phase peptide synthesis (SPPS). This is an important factor to consider when planning to synthesize peptides containing unnatural amino acids (e.g. D-amino acids) or when there is a need for large scale peptide synthesis. Secondly, in the case of ionic liquid supported synthesis, every intermediate could be readily purified by repeated solvent washings (liquid/liquid phase separation). In this aspect, ILSS resembles FPPS (fluorous phase peptide synthesis) as well as SPSPS (soluble polymer supported peptide synthesis).

In the case of ILSS, the separation process is not as easily automated as is the case for SPPS which involves solid/liquid phase separation. However, the loading capacity for ILSS is higher than for SPPS since only about a one molar equivalent of the low molecular weight ionic liquid 1 is generally required. Moreover, the cost of an ionic liquid support is generally lower than that of a fluorous support or even that of a solid polymer support, which is a further important consideration when planning a large scale peptide synthesis. Finally, in the case of ILSS, the structure and purity of each intermediate in the synthesis was easily verifiable by routine spectroscopic methods (i.e. $^1$H, $^{13}$C NMR and MS).

EXAMPLE 3

Ionic Liquid Supported Oligosaccharide Synthesis

As illustrated hereinbelow in Scheme 4, the synthesis of an oligosaccharide using ionic liquid supported methods was conveniently achieved using simple phase separations and without the need of chromatographic methods for product purification.

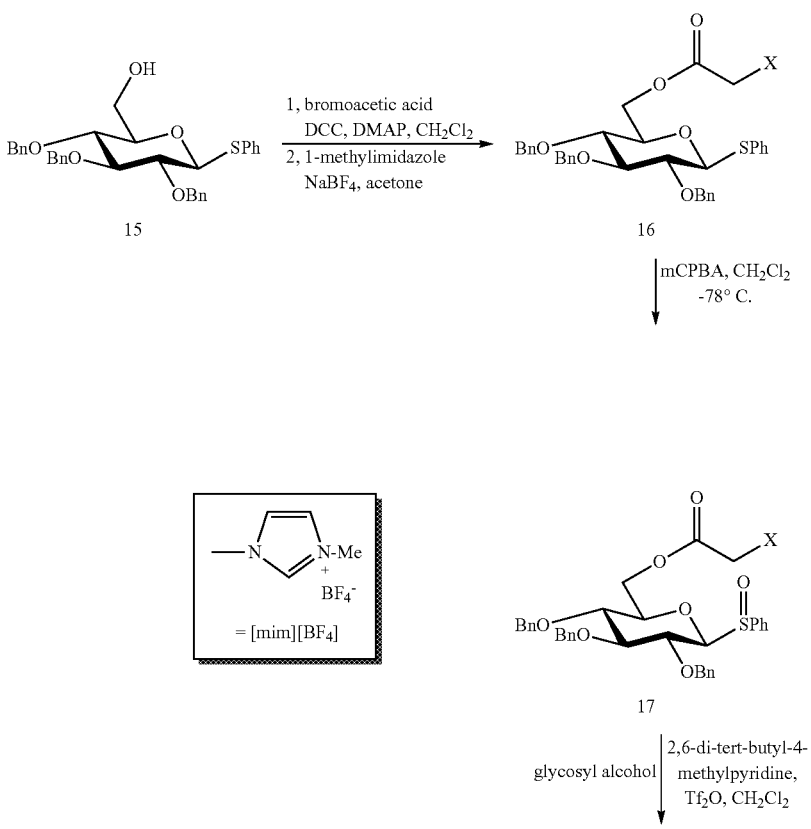

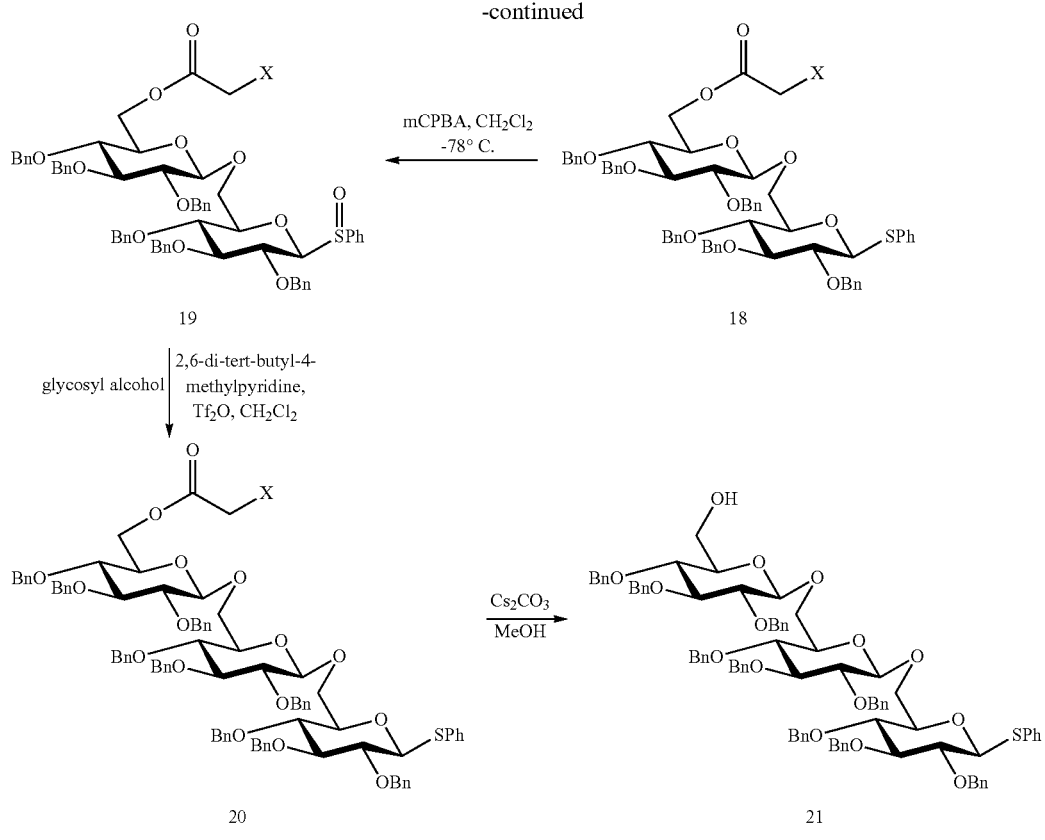

a X = Br,
b X = [mim][BF$_4$]
c X = H

The β-thioglycoside 15, prepared from modified literature procedures,[43] starting from phenyl 2,3,4,6-tetra-O-acetyl-1-thio-β-D-glucopyranoside, was acylated with bromoacetic acid/DCC/DMAP in CH$_2$Cl$_2$ at room temperature to give the bromoacetate 16a (X=Br) (Scheme 4).

Reaction of 16a (X=Br) with 1-methylimidazole and sodium tetrafluoroborate in acetone at room temperature gave the ionic liquid anchored saccharide 16b (X=[mim][BF$_4$]) in 98% yield. Compound 16b was purified by first washing the crude product with diethyl ether to remove excess 1-methylimidazole. The product was then dissolved in CH$_2$Cl$_2$ and the insoluble inorganic NaBr salt generated in the reaction was removed simply by filtration. The structure of 16b was confirmed by NMR ($^1$H, $^{13}$C, COSY and HMQC) spectroscopy, which clearly showed the presence of the imidazolium moiety and the anomeric carbon as the β-anomer. The electrospray ionization mass spectrum (ESI-MS) of 16b showed the presence of the cation as the only molecular ion.

The monosaccharide 16b was then oxidized by m-chloroperbenzoic acid in CH$_2$Cl$_2$ at −78° C. for 20 minutes to give the sulfoxide 17b (X=[mim][BF$_4$]) as a mixture of diastereomers (due to sulfoxide chirality) in 97% yield. The other product of the reaction, m-chlorobenzoic acid was removed from the crude product mixture by washing with di-isopropyl ether.

The sulfoxide glycosylation reaction was then used as the sugar-sugar assembling method[44-46] with 17b as the glycosyl donor and 15 as the acceptor (3 equiv). The coupling reaction using 2,6-di-tert-butyl-4-methylpyridine (4 equiv) and Tf$_2$O (1 equiv) was conducted in dry CH$_2$Cl$_2$ at −78° C. because both the glycosyl donor and acceptor were well soluble in dichloromethane at low temperature. The reaction process was monitored by TLC.

The product disaccharide 18b (X=[mim][BF$_4$]) was obtained by washing away the excess glycosyl alcohol 15, the acid scavenger base, and other side-products with n-pentane and then with di-isopropyl ether. The protonated acid scavenger, 2,6-di-tert-butyl-4-methylpyridinium triflate, was removed from 18b by adding n-pentane to a solution of crude 18b in CH$_2$CO$_2$, followed by cooling the solution to allow 17b to phase-separate from the solution. The ionic liquid-bound disaccharide 18b was obtained in high purity as indicated by HMQC NMR spectroscopy showing the two anomeric carbons. Furthermore, EIS-MS not only confirmed the disaccharide structure, but also showed the absence of any unreacted monosaccharide. Repetition of the same sequence of reactions gave the sulfoxide 19b and then the ionic liquid bound trisaccharide 20b (X=[mim][BF$_4$]). The formation of the trisaccharide was confirmed by HMQC NMR spectroscopy, showing the presence of three anomeric carbons and by ESI-MS, clearly indicating the trisaccharide cation without any contamination of the mono- or disaccharides.

The ionic liquid moiety and the linker were easily cleaved from 20b by using one equivalent of Cs$_2$CO$_3$ in methanol, to quantitatively afford the product 21. The trisaccharide 21 was easily isolated by evaporation of the methanol solvent and dissolving the crude product in CH$_2$Cl$_2$ followed by filtration to remove the imidazolium salts. The trisaccharide 21, thus obtained without any chromatographic or other purification procedures, was found to be NMR and TLC pure. Its HMQC NMR spectrum and ESI-MS (M+Na$^+$=1429.7) were found to be identical to an authentic sample of 21, prepared independently by classical solution phase synthesis starting with 16c (X=H), following the same sequence of reactions as illustrated in Scheme 4 but with chromatographic purification following each of the reaction steps. The good purity of 21 as obtained by the ILSS approach in comparison with the classical solution phase synthesis through 16c, suggests that the coupling conditions and stereoselectivity developed for classical solution phase synthesis can be translated to ILSS. The present example also presents a contrast to the solid-phase synthesis where chromatography is generally necessary to purify the final product after cleavage from the solid-phase support.[47]

EXAMPLE 4

Ionic Liquid Supported Oligonucleotide Synthesis

Solid-phase synthesis of oligonucleotides using the phosphoramidite method[2-6] is an iterative process in which a solid support with an attached nucleoside is deblocked at the terminus by removing a labile protecting group, thus liberating a nucleophilic hydroxyl group. This terminal nucleophile is then allowed to couple to a protected phosphoramidite monomer in the presence of an activator. The newly created phosphite triester linkage is then oxidized to provide the desired and more stable phosphate triester. This process is repeated until an oligomer of the desired length and composition is obtained. The same iterative methodology may be used when soluble supports are employed.

3-Hydroxyethyl-(1-methylimidazolium)-tetrafluoroborate (1), readily available from the reaction of 1-methylimidazole and 2-bromoethanol[35a-d] was chosen as a non-limiting example of a suitable ionic liquid support to illustrate the ionic liquid supported oligonucleotide synthesis as contemplated by the present invention. Other ionic liquid supports capable of being used in accordance with the present invention are known in the art and are within the capacity of a skilled technician.

The succinylated 5'-MMT-deoxynucleoside 23[48] is coupled to the ionic liquid 1 using dicyclohexylcarbodiimide (DCC) and catalytic amounts of 4-dimethylaminopyridine (DMAP) in acetonitrile to give the ionic liquid supported nucleoside 24 (Scheme 5). The reaction mixture is filtered to remove the insoluble dicyclohexylurea (DCU) byproduct formed during the reaction. Compound 24 is then isolated and purified by adding the reaction mixture dropwise to a stirred diethyl ether-ethyl acetate solution. The resulting precipitate, composed of underivatized ionic liquid 1 and the desired product 24, is then taken up in chloroform and extracted with water. The ionic liquid 1 is removed with the aqueous phase while the desired product 24 remains in the organic phase due to the hydrophobicity of the monomethoxytrityl protecting group attached at the 5' position of thymidine. Though the 5'-monomethoxytrityl (MMT) thymidine derivative was used in this case, the more commonly used 5'-dimethoxytrityl (DMT) thymidine derivative may be easily substituted during this step. Removal of the solvent yields the ionic liquid derivatized nucleoside 24 in reasonable yield. The structure of 24 was confirmed by $^1$H NMR and electrospray ionization mass spectrometry (ESI-MS).

Detritylation of compound 24 is achieved by the addition of 3% trifluoroacetic acid in acetonitrile and stirring for 20 minutes at room temperature. The product is quickly isolated and purified by adding the reaction mixture dropwise to a stirred ethyl ether-ethyl acetate solution and collecting the precipitate. Occasionally redissolution in the acid solution and a second precipitation is required to complete the deprotection and to entirely remove residual tritanol. Compound 25 is obtained as a light brown foam in 96% yield, its structure and purity verified by $^1$H NMR and ESI-MS.

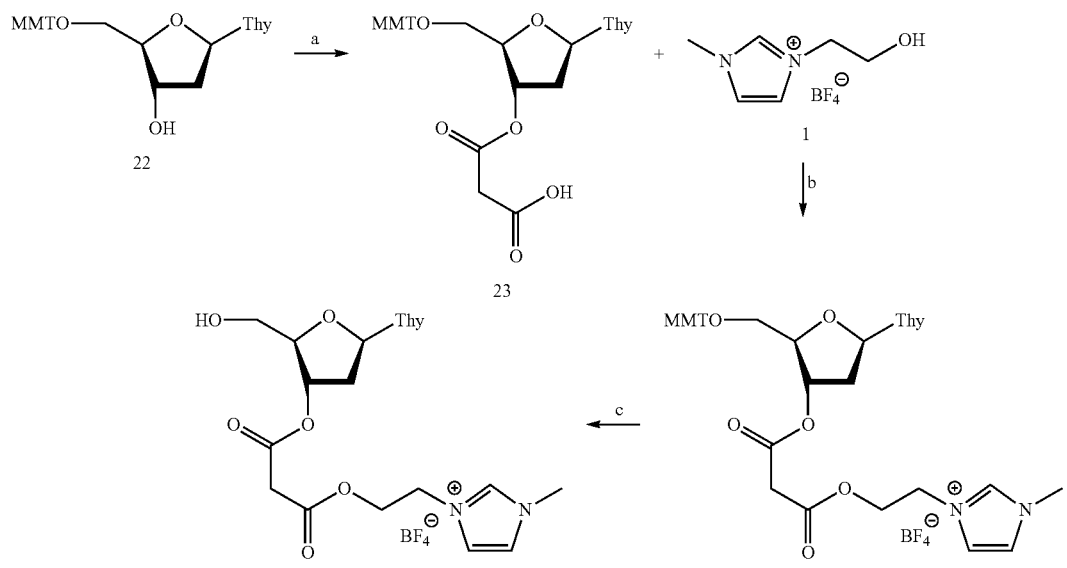

Scheme 5 a) Pyridine, DMAP, Succinic anhydride 2 days room temperature, b) DCC, DMAP, Acetonitrile 3 days room temperature, c) 3% trifluoroacetic acid in dichloromethane or acetonitrile.

The dinucleoside phosphotriesters ApT, CpT, GpT, and TpT (27a-d)[49] (Scheme 6) are prepared at the 250 μmol scale by reacting the ionic liquid supported nucleoside 25 with a 1.5-fold excess of the appropriate phosphoramidite derivatives (26a-d) using 4,5-dicyanoimidazole (DCI) as the activating agent in THF or acetonitrile and stirring for 1 to 2 hours. After the reaction has come to completion, the excess activated phosphoramidite is quenched through the addition of an excess of anhydrous ethanol and a further 10 minutes of stirring. Quenching the phosphoramidites facilitates their removal during purification. The dinucleoside phosphite triester intermediates are then isolated simply by precipitating from ethyl acetate:ethyl ether (1:9) at room temperature, prior to oxidation. It was found that the quenched excess mononucleoside 3'-O-phosphoramidite is much more soluble in ethyl acetate/ether than the coupled product, thus making its removal from the dinucleoside phosphite triester possible. Generally, the precipitate is dissolved directly off of the filter using acetonitrile or methanol and precipitated again from 1:9 ethyl acetate: ethyl ether in order to enhance the purity of the desired product.

To carry out the oxidation of the phosphite triester intermediates, the collected precipitate is again dissolved in a small amount of acetonitrile, followed by the addition of a small excess of pyridine and a large excess of a 0.1M solution of iodine in 2:1 tetrahydrofuran (THF):water. Once the persistence of a color (due to iodine) is established, aqueous sodium bisulphite (5%) is added to reduce the excess iodine. The reaction mixture is then diluted with chloroform and extracted with water. The aqueous layer comprises the resultant salts (NaI, $Na_2SO_4$, excess bisulphite, pyridinium iodide, etc) in addition to any uncoupled ionic liquid supported nucleoside(tide) since it lacks a terminal trityl group, rendering it water soluble. Removal of the organic solvent under reduced pressure yields the products (27a-d) as light brown foams in good yield (Table 4) and high purity, eliminating the need for a capping step. Detritylation of 27a-d is achieved by the addition of 3% trifluoroacetic acid (TFA) in dichloromethane or acetonitrile, stirring for 20 minutes and precipitation in ethyl acetate: ethyl ether (1:9). The material obtained at this point may contain up to 5% of tritylated starting material, resulting from the equilibrium established during this step (ROH+ $DMT^+$=DMT-OR). Quenching with ethanol to trap the DMT cation did not seem to eliminate this problem. However, the purity is significantly enhanced (no tritylated product observed by low resolution ESI-MS in the bulk product), if the TFA treatment is repeated, (i.e. redissolution of the precipitate in 3% trifluoroacetic acid solution, followed by a second precipitation). The purified products are simply filtered off, yielding off-white to light yellow powdery solids in high yields (Table 4). The collected solids (28a-d) are now ready for another round of coupling or, if the desired sequence is complete, deprotection.

Scheme 6

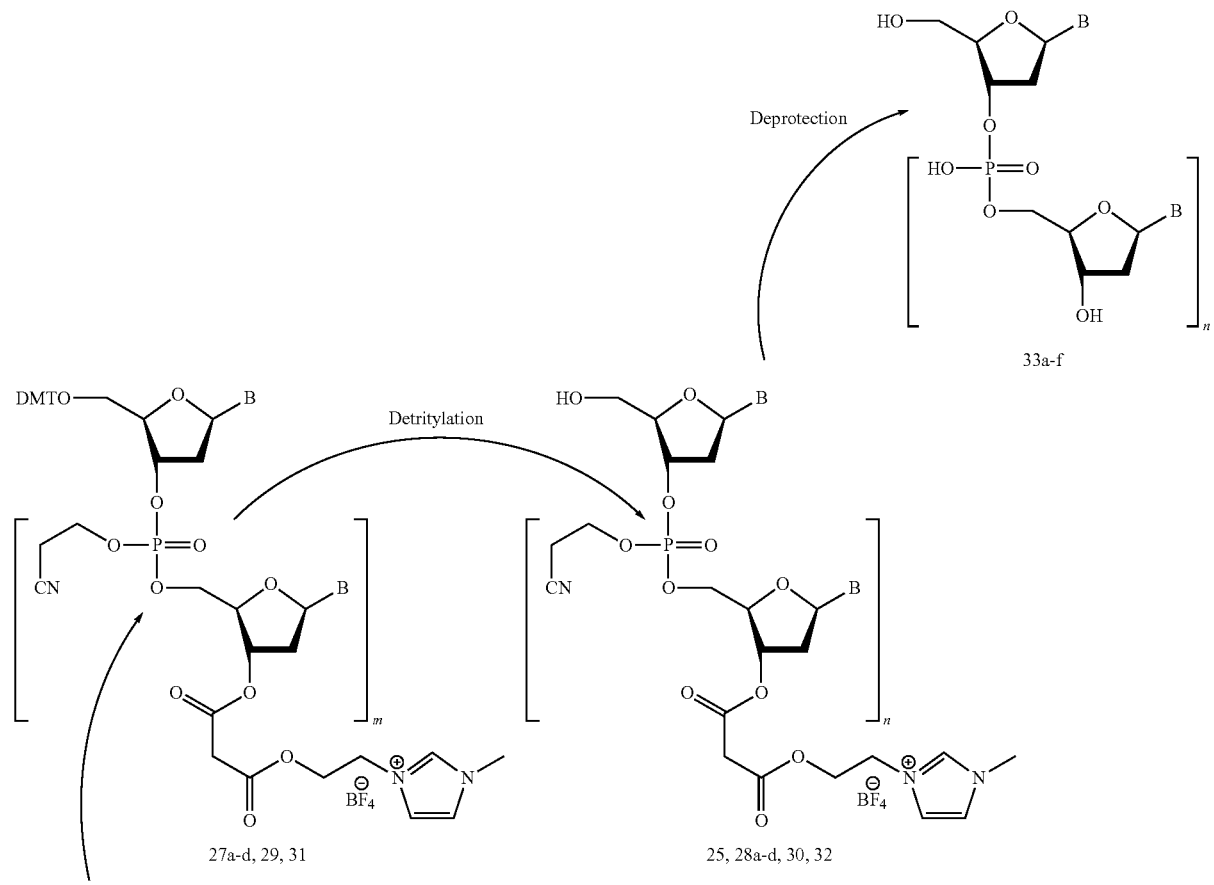

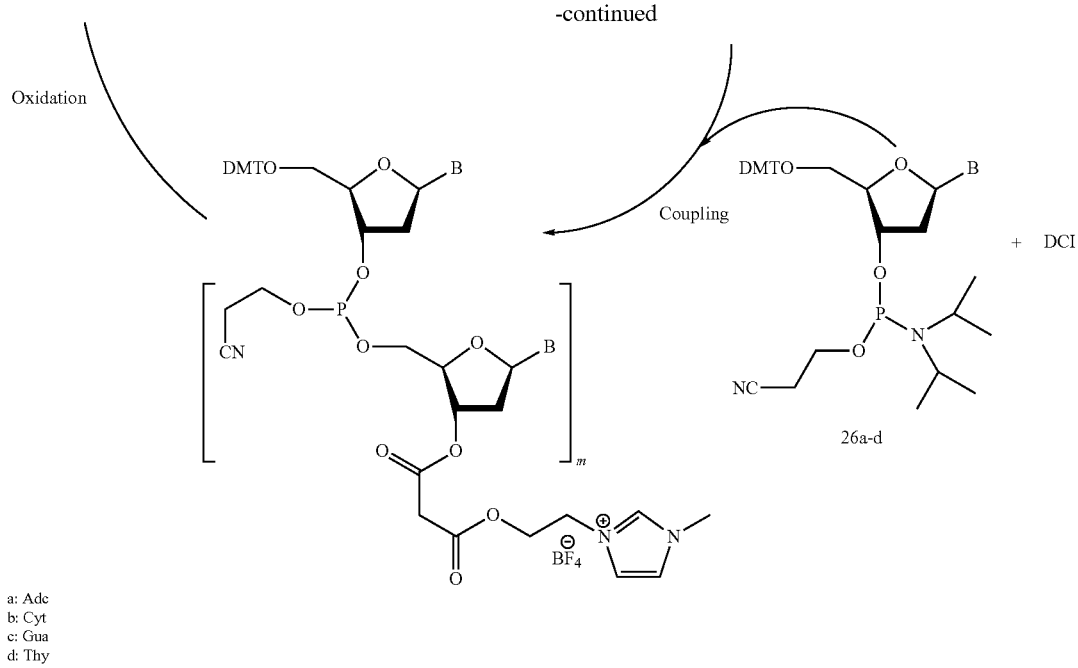

a: Ade
b: Cyt
c: Gua
d: Thy

In addition to the dimers 28a-d described above, a thymidine trimer (29, 30) and a tetramer (31, 32) were also synthesized at the 50-100 μmol scale. The identities of the ionic liquid supported compounds were confirmed by $^{31}$P-NMR and both low and high-resolution ESI-MS (Table 4). The $^{31}$P NMR data (Table 4) for the dimeric species reveal two signals corresponding to the two possible Rp and Sp diastereomeric phosphotriesters. When the β-cyanoethyl phosphate protecting group is removed, the internucleotide linkage becomes achiral and only a single signal is observed. Likewise, the $^{31}$P-NMR data (Table 4) for the trimeric species reveal eight signals (4 diastereoisomers each exhibiting 2 signals) when the trityl protecting group is still attached. Once the trityl group is removed the signals can no longer be resolved. This is also the case for the tetramer where the expected number of diastereoisomers is 8 ($2^3 \times 3$=24 peaks). The fact that the isolated compounds are present as diastereomeric pairs also complicates the assignments of $^1$H NMR peaks. However, with the use of a $^{31}$P tuned CIGAR experiment it was possible to observe the expected 3'-5' connectivity through the phosphotriester linkage.

Figure 7:
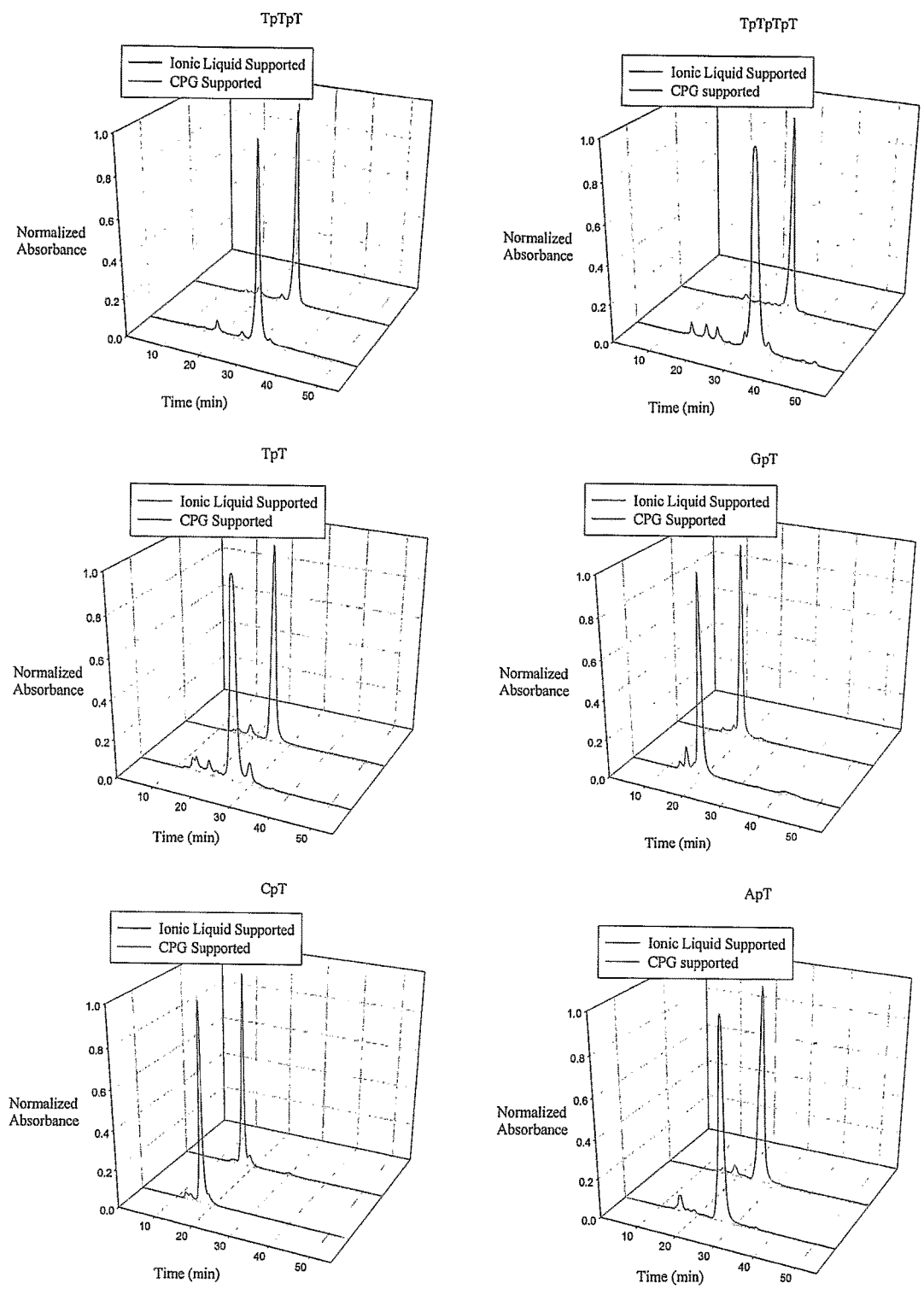
FIG. 7 is an illustration of various HPLC chromatographs of deprotected oligonucleotides.

The oligonucleotides synthesized above were compared to those synthesized on controlled pore glass (CPG; 1 μmol scale), a commonly used solid support, using identical sequences and the two systems were deprotected in parallel. Complete deprotection of the desired oligonucleotides is achieved by treating them with concentrated ammonium hydroxide/ethanol for 48 hours at room temperature or 16 hours at 60° C. These conditions ensure complete cleavage of the cyanoethyl protecting group, the ionic liquid moiety, any protection of the exocyclic amines of the bases (Ade, Cyt and Gua), and the monosuccinate linker. The oligonucleotides were isolated by removal of the ethanol and ammonium hydroxide solution under vacuum, redissolution in water (the solid support is simply settled by centrifugation for the CPG supported oligomers) and then chromatographic purification by ion-pairing reverse phase HPLC, anion-exchange HPLC or polyacrylamide gel electrophoresis. The products of the ILSS procedure were compared via LCMS to those obtained through the standard gene machine synthesis techniques. FIG. 7 shows the comparison of oligomers grown on an ionic liquid (IL) support and those grown on CPG. The LCMS data are summarized hereinbelow in Table 5.

TABLE 4

Recovery and Physical Data for Ionic Liquid Supported Oligonucleotides

| Compound | Sequence | % Recovery | $^{31}$P NMR (ppm) | m/z (experimental) | m/z (calculated) |
|---|---|---|---|---|---|
| 27a | $^{DMT}$ApT | 89 | −1.324, −1.477 | 1223.4 | 1223.4 |
| 27b | $^{DMT}$CpT | 91 | −1.545, −1.754 | 1199.4 | 1199.4 |
| 27c | $^{DMT}$GpT | 90 | −1.149, −1.194 | 1205.6 | 1205.4 |
| 27d | $^{DMT}$TpT | 91 | −1.494, −1.584 | 1110.4 | 1110.4 |
| 28a | $^{HO}$ApT | 93 | −1.176, −1.516 | 921.4 | 921.3 |
| 28b | $^{HO}$CpT | 95 | −1.381, −1.613 | 897.3 | 897.3 |
| 28c | $^{HO}$GpT | 96 | −1.047, −1.064 | 903.4 | 903.3 |
| 28d | $^{HO}$TpT | 78 | −1.188, −1.284 | 808.3 | 808.3 |
| 29 | $^{DMT}$TpTpT | 92 | −1.081 to −1.477 | 1467.5 | 1467.8 |
| 30 | $^{HO}$TpTpT | 98 | −1.157 to −1.531 | 1165.2 | 1165.3 |
| 31 | $^{DMT}$TpTpTpT | 89 | −1.169 to −1.859 | 1824.2 | 1824.5 |
| 32 | $^{HO}$TpTpTpT | 100 | −1.142 to −1.51 | 1522.4 | 1522.4 |

TABLE 5

HPLC/MS Analysis of Deprotected Oligonucleotides

| Sequence | Synthetic Support | Retention Time (min) | % Total Area | Low Resolution MS (-ve mode) |
|---|---|---|---|---|
| ApT | IL | 26.3 | 93.8 | 554.2 |
|  | CPG | 26.3 | 96.1 | 554.2 |
| CpT | IL | 16.7 | 87.8 | 530.2 |
|  | CPG | 16.8 | 89.5 | 530.2 |
| GpT | IL | 19.0 | 89.1 | 570.2 |
|  | CPG | 18.9 | 95.1 | 570.2 |
| TpT | IL | 25.3 | 88.1 | 545.2 |
|  | CPG | 25.3 | 92.5 | 545.2 |
| TpTpT | IL | 29.9 | 92.1 | 849.1 |
|  | CPG | 29.5 | 94.0 | 849.2 |
| TpTpTpT | IL | 32.4 | 85.5 | 1153.2 |
|  | CPG | 31.9 | 90.5 | 1153.2 |

In all cases, the retention times of the IL generated oligonucleotide material correlate well with the CPG generated oligomer. The area percent of the principal peak for the IL oligomers is always several percentage points above that of the CPG derived oligomers. However, this is somewhat misleading taking into consideration that the ionic liquid itself (retention time 11.2 min; $\lambda_{max}$ 217 nm) absorbs weakly at the wavelength used to monitor the oligomers. Omitting the area due to the ionic liquid derived peaks brings the values of the IL derived oligomers in line with those obtained for those synthesized on CPG. Thymidine nucleoside, which is visible in several of the HPLC traces, arises from incomplete coupling or partial detritylation of the solid support prior to the initial capping step, and elutes at approximately 19 minutes. Though normally present in materials synthesized on CPG, the post-oxidation extraction largely removes this material from the IL mediated products (FIG. 1). As described earlier, the presence of failure sequences in the trimer and tetramer (the so called "n-1" peaks) are likely not due to incomplete coupling but rather due to incomplete detritylation prior to coupling. This material would not be removed during the extraction and would be deblocked after the detritylation subsequent to coupling (i.e. after a trimer synthesis, the detritylation would yield the desired trimer and an unwanted dimer carried from the previous step). It is therefore important to ensure complete detritylation prior to each coupling step.

Experimental.

General. All reagents were obtained commercially and were used without further purification unless otherwise noted. Solvents were of reagent grade and if necessary, were dried by standard procedures. Reactions were performed under anhydrous conditions except otherwise specially indicated and monitored by thin-layer chromatography (TLC) on silica gel 60 F-254 polyester-backed plates (250 μm thick), detecting under UV light (254 nm) or charring with aqueous potassium permanganate solution. $^1$H NMR and $^{13}$C NMR spectra were recorded on a Varian Mercury-300 (300 MHz) or a Mercury-400 (400 MHz) spectrometer at 20° C. (oligopeptide synthesis). $^1$H and $^{13}$C NMR, HMQC NMR, COSY NMR spectra were recorded on Unity 500, Varian Mercury 400 and Varian Mercury 300 spectrometers equipped with Sun workstations (oligosaccharide synthesis). The chemical shifts were reported in parts per million on the δ scale referenced to residue CHCl$_3$ at δ 7.24 ppm, H$_2$O at 4.67 ppm, acetone at 2.06 or methanol at 3.30 for $^1$H NMR, and CHCl$_3$ at 77.0 ppm, methanol at 49.0 ppm and acetone at 29.8 ppm for $^{13}$C NMR. The proton and carbon assignments were made by standard gHMQC and gCOSY experiments. Melting points were taken via melting point apparatus without correcting the thermometer. The electron spray ionization (ESI) mass spectra were recorded on KRATOS MS25RFA Mass Spectrometer. High resolution mass analyses were performed on a VG MICROMASS ZAB 2F HS spectrometer (FAB). Oligonucleotide high resolution mass spectra measurements were conducted in positive ion electrospray mode with an IonSpec 7.0 tesla FTMS, calibrated with polyethylene glycol 300, 600 and 1000. Optical rotations were determined using a DIP-140 (JASCO) digital polarimeter, Degrees of racemization and purity of the final product were determined by analytical HPLC using Diacel Chiralcel OD-H, OD-J chiral analytical columns with 2-propanol in hexanes as the eluent, and Zorbax SB-CN Semi-prep columns with CH$_3$CN/H$_2$O/TFA as the eluent system.

Oligonucleotide synthesis, purification and identity confirmation. Oligonucleotides were purified after cleavage from their respective supports by reverse phase high-performance liquid chromatography (HPLC). Separations were achieved using a Polymerex 10μ RP-1 column (Phenomenex, 10 mm×250 mm, 10μ packing) heated to 60° C., with a mobile phase flow rate of 1 mL/min generated by a Waters 1525 binary HPLC pump. The initial mobile phase was comprised of an isocratic flow of 100 mM triethylammonium acetate buffer (pH 7.0, 80:20 (v/v) water:methanol) for 2 minutes followed by a gradient shift to 100 mM triethylammonium acetate buffer (pH 7.0, 70:30 (v/v) water:methanol) over a 35 minute period followed by 1 minute of isocratic flow before a 14 minute gradient switch back to initial condition and ending with a 5 minute period of isocratic flow. The elution was monitored on a Waters 2487 dual absorbance detector at 260 nm and 217 nm. Fractions of the eluting peaks were collected and the mobile phase was removed under vacuum. The samples were redissolved in 10% methanol-water and the molecular weights were subsequently determined by low-resolution electrospray ionization mass-spectrometry on a ThermoQuest Finnigan LCQ Duo mass spectrometer in the negative ion mode. Solid phase synthesis of oligonucleotides was carried out on a 1 μmol scale on 500 Å long chain alkyl amine derivatized controlled pore glass (LCAA-CPG) using an Applied Biosystems 3400 DNA/RNA synthesizer as described previously using standard conditions.[6]

The esterification (loading) step. To a mixture of ionic liquid 1 (1.07 g, 5 mmol), Boc-leucine (L- or D-form 2.31 g, 10 mmol) and dimethylaminopyridine (0.25 g, 2 mmol) in dry acetonitrile (25 mL) was added dicyclohexylcarbodiimide (DCC, 1M in CH$_2$Cl$_2$, 10 mL, 10 mmol). The mixture was stirred vigorously for 18 h at room temperature under nitrogen and filtrated through a Celite™ plug. The Celite™ plug was rinsed with acetonitrile and the combined organic phase was concentrated under vacuum. The crude residue was washed firstly with ether (20 mL×3), then dissolved in CH$_2$Cl$_2$ and washed with 2M HCl (10 mL×3). The organic phase was dried over Na$_2$SO$_4$ and concentrated to afford ionic liquid supported Boc-leucine 2a (L-isomer) or 2b (D-isomer) 1.95 g (91%) as pale yellow oils. $^1$H NMR (300 MHz, Acetone-d$_6$) δ 9.08 (s, 1H), 7.80 (s, 1H), 7.71 (s, 1H), 6.41 (d, br, J=7.8 Hz, 1H), 4.66-4.64 (m, 2H), 4.60-4.43 (m, 2H), 4.20-4.13 (m, 1H), 4.04 (s, 3H), 1.68-1.53 (m, 3H), 1.39 (s, 9H), 0.91 (d, J=6.0 Hz, 3H), 0.89 (d, J=6.0 Hz, 3H); $^{13}$C NMR (100 MHz, Acetone-d$_6$) δ 173.2, 156.4, 138.0, 124.4, 123.6, 79.3, 63.4, 53.0, 49.3, 40.7, 36.6, 28.5 (3C), 25.4, 23.1, 21.6; HRMS (FAB) calcd. for C$_{17}$H$_{30}$N$_3$O$_4$ (M$^+$) 340.2237, found 340.2236.

Peptide formation; coupling and deprotection steps. To a solution of ionic liquid supported Boc-peptide (2 mmol) in CH$_2$Cl$_2$ (10 mL) was added TFA (10 mL). The reaction mixture was stirred at room temperature under nitrogen for 0.5 h. Upon concentration under reduced pressure, the residue was washed twice with ether and dried under vacuum to yield the deprotected ionic liquid supported peptide as a TFA salt. The residue was then dissolved, together with the next Boc-protected amino acid (3 mmol) and PyBOP (3 mmol), in CH$_3$CN (35 mL). DIPEA (6 mmol) was added dropwise and the resulting reaction mixture was stirred at 35° C. under a nitrogen atmosphere for 8 h. The solvent was removed under vacuum and the residue was washed firstly with ether (20 mL×3), then dissolved in CH$_2$Cl$_2$ and washed with water (10 mL×3). The organic phase was dried over Na$_2$SO$_4$ and concentrated to afford the ionic liquid supported Boc-peptide (90% yield) which was of sufficient purity to be used directly for the next cycle of the peptide synthesis. The product could be further purified, if desired, by dissolving the compound in acetone, filtering through a short pad of silica gel, and evaporating the solvent.

Ionic liquid supported leucine TFA salt 3a: $^1$H NMR (400 MHz, Acetone-d$_6$) δ 9.20 (s, 0.55H), 9.12 (s, 0.45H), 7.85 (s, 1H), 7.68 (s, 1H), 5.02-4.98 (m, 0.45H), 4.75-4.58 (m, 4H), 4.27-4.25 (m, 0.55H), 4.05 (s, 3H), 1.90-1.87 (m, 2H), 1.73-1.70 (m, 1H), 0.95 (d, J=6.0 Hz, 3H), 0.93 (d, J=6.0 Hz, 3H); $^{13}$C NMR (100 MHz, Acetone-d$_6$) δ 169.4 (0.55C), 167.7 (0.45C), 138.0 (0.55C), 137.8 (0.45C), 124.4, 123.6 (0.45C), 123.5 (0.55C), 65.1 (0.45C), 64.9 (0.55C), 52.2, 48.9, 39.8 (0.55C), 39.4 (0.45C), 36.4, 25.1 (0.45C), 24.8 (0.55C), 22.7 (0.45C), 22.3 (0.55C), 22.1 (0.55C), 21.6 (0.45C); HRMS (FAB) calcd. for C$_{24}$H$_{44}$N$_6$O$_4$BF$_4$ (2M$^+$+BF$_4^-$) 567.3450, found 567.3453.

Ionic liquid supported Leu-Boc-phenylalanine 4a: foam-like pale yellow solids; $^1$H NMR (400 MHz, Acetone-d$_6$) δ 9.04 (s, 1H), 7.81 (s, 1H), 7.70 (s, 1H), 7.67 (d, br, J=6.8 Hz, 1H), 7.29-7.20 (m, 5H), 6.20 (d, br, J=8.0 Hz, 1H), 4.69-4.66 (m, 2H), 4.64-4.52 (m, 2H), 4.44-4.37 (m, 2H), 4.08 (s, 3H), 3.19-2.91 (m, 2H), 1.72-1.58 (m, 3H), 1.35 (s, 9H), 0.92 (d, J=6.0 Hz, 3H), 0.89 (d, J=6.0 Hz, 3H); $^{13}$C NMR (100 MHz, Acetone-d$_6$) δ 172.9, 172.4, 156.5, 138.2, 132.6, 129.9 (2C), 128.8 (2C), 127.0, 124.5, 123.5, 79.4, 63.4, 56.6, 51.6, 49.4, 40.4, 38.3, 36.7, 28.4 (3C), 25.2, 23.2, 21.6; HRMS (FAB) calcd. for C$_{26}$H$_{39}$N$_4$O$_5$ (M$^+$) 487.2920, found 487.2920. Treatment with trifluoroacetic acid afforded the ionic liquid supported Leu-phenylalanine TFA salt 6: $^1$H NMR (300 MHz, Acetone-d$_6$) δ 9.33 (s, br, 0.6H), 9.25 (s, br, 0.4H), 7.87 (s, br, 1H), 7.72 (s, br, 0.6H), 7.67 (s, br, 0.4H), 7.28-7.25 (m, 5H), 5.38-5.33 (m, 0.4H), 4.70-4.50 (m, 4H), 4.40-4.34 (m, 1.6H), 4.07 (s, 1.8H), 4.00 (s, 1.2H), 3.55-3.26 (m, 2H), 1.82-1.70 (m, 2H), 1.58-1.53 (m, 1H), 0.92 (d, J=6.0 Hz, 3H), 0.87 (d, J=6.0 Hz, 3H); $^{13}$C NMR (75 MHz, Acetone-d$_6$) δ 172.2, 172.0, 138.7 (0.6C), 138.5 (0.4C), 136.5 (0.6C), 135.6 (0.4C), 130.5 (0.8C), 130.4 (1.2C), 129.3 (1.2C), 129.2 (0.8C), 128.0 (0.6C), 127.9 (0.4C), 124.5, 123.6 (0.4C), 123.5 (0.6C), 63.6 (0.4C), 63.5 (0.6C), 54.9, 52.1 (0.6C), 52.0 (0.4C), 49.5 (0.6C), 49.4 (0.4C), 40.3 (0.4C), 39.9 (0.6C), 38.2 (0.6C), 37.4 (0.4C), 36.6, 25.2 (0.6C), 25.1 (0.4C), 23.1, 21.6 (0.4C), 21.5 (0.6C); HRMS (FAB) calcd. for C$_{21}$H$_{31}$N$_4$O$_3$ (M$^+$) 387.2395, found 387.2396.

Ionic liquid supported Leu-Phe-Boc-glycine 7: foam-like pale yellow solids; $^1$H NMR (300 MHz, Acetone-d$_6$) δ 9.04 (s, 1H), 7.78 (t, J=1.8 Hz, 1H), 7.66 (t, J=1.8 Hz, 1H), 7.62 (d, J=7.5 Hz, 1H), 7.55 (d, J=8.1 Hz, 1H), 7.30-7.18 (m, 5H), 6.46 (m, 1H), 4.73-4.65 (m, 3H), 4.54-4.51 (m, 2H), 4.45-4.38 (m, 2H), 4.06 (s, 3H), 3.78-3.61 (m, 2H), 3.24-3.00 (m, 2H), 1.71-1.56 (m, 3H), 1.39 (s, 9H), 0.90 (d, J=6.0 Hz, 3H), 0.88 (d, J=6.0 Hz, 3H); $^{13}$C NMR (75 MHz, Acetone-d$_6$) δ 171.7 (2C), 170.3, 156.7, 137.7, 137.5, 129.4 (2C), 128.6 (2C), 126.8, 124.1, 123.0, 79.3, 63.1, 54.9, 51.3, 48.9, 44.4, 39.9, 37.4, 36.2, 28.0 (3C), 24.7, 22.7, 21.2; HRMS (FAB) calcd. for C$_{28}$H$_{42}$N$_5$O$_6$ (M$^+$) 544.3134, found 544.3135. Treatment with trifluoroacetic acid afforded the ionic liquid supported Leu-Phe-glycine TFA salt 8: $^1$H NMR (300 MHz, Acetone-d$_6$) δ 9.13 (s, 1H), 7.80 (s, 1H), 7.68 (s, 1H), 7.32-7.20 (m, 5H), 4.66-4.50 (m, 7H), 4.41-4.39 (m, 1H), 4.06 (s, 3H), 3.25-2.96 (m, 2H), 1.77-1.68 (m, 2H), 1.59-1.54 (m, 1H), 0.92 (d, J=6.0 Hz, 3H), 0.87 (d, J=6.0 Hz, 3H); $^{13}$C NMR (75 MHz, Acetone-d$_6$) δ 172.4, 172.3, 172.2, 138.4 (0.5C), 138.3 (0.5C), 138.2 (0.5C), 138.0 (0.5C), 130.0 (2C), 128.94 (1C), 128.91 (IC), 127.22 (0.5C), 127.17 (0.5C), 124.57 (0.5C), 124.54 (0.5C), 123.44 (0.5C), 123.40 (0.5C), 63.4, 56.8 (0.5C), 56.6 (0.5C), 51.6 (0.5C), 51.5 (0.5C), 49.5 (0.5C), 49.3 (0.5C), 42.8, 39.9 (0.5C), 39.8 (0.5C), 38.4 (0.5C), 38.3 (0.5C), 36.6, 25.2 (0.5C), 25.16 (0.5C), 23.17 (0.5C), 23.15 (0.5C), 21.5 (0.5C), 21.4 (0.5C); HRMS (FAB) calcd. for C$_{23}$H$_{34}$N$_5$O$_4$ (M$^+$) 444.2609, found 444.2611.

Ionic liquid supported Leu-Phe-Gly-Boc-glycine 9: foam-like pale yellow solids; $^1$H NMR (300 MHz, Acetone-d$_6$) δ 9.09 (s, 1H), 8.12 (m, br, 1H), 7.80 (t, J=1.8 Hz, 1H), 7.68 (t, J=1.8 Hz, 1H), 7.64 (m, 1H), 7.61 (m, 1H), 7.30-7.21 (m, 5H), 6.57 (m, 1H), 4.76-4.59 (m, 3H), 4.54-4.51 (m, 2H), 4.40-4.33 (m, 1H), 4.08 (s, 3H), 3.82-3.75 (m, 4H), 3.33-2.95 (m, 2H), 1.89-1.55 (m, 3H), 1.43 (s, 9H), 0.94 (d, J=6.0 Hz, 3H), 0.89 (d, J=6.0 Hz, 3H); $^{13}$C NMR (100 MHz, Acetone-d$_6$) δ 171.9, 171.8, 171.6, 169.8, 156.9, 138.0, 137.8, 129.1 (2C), 128.6 (2C), 126.7, 124.1, 123.0, 79.4, 63.1, 55.6, 51.4, 48.9, 44.6, 43.8, 39.9, 37.3, 36.3, 28.2 (3C), 24.7, 22.9, 21.2; HRMS (FAB) calcd. for C$_{30}$H$_{45}$N$_6$O$_7$ (M$^+$) 601.3348, found 601.3350. Treatment with trifluoroacetic acid afforded the ionic liquid supported Leu-Phe-Gly-glycine TFA salt 10: $^1$H NMR (400 MHz, Acetone-d$_6$) δ 9.10 (s, 1H), 7.81 (s, 1H), 7.70 (s, 1H), 7.28-7.20 (m, 5H), 4.75-4.67 (m, 5H), 4.58-4.50 (m, 2H), 4.43-4.38 (m, 1H), 4.08 (s, 3H), 3.89-2.87 (m, 2H), 3.23-3.04 (m, 2H), 1.65-1.58 (m, 3H), 0.92 (d, J=6.0 Hz, 3H), 0.87 (d, J=6.0 Hz, 3H); $^{13}$C NMR (100 MHz, Acetone-d$_6$) δ 171.9, 171.7, 137.9, 129.4, 129.3 (2C), 128.4 (2C), 126.7, 124.0, 123.0, 63.0, 55.8, 50.8, 49.3, 48.9, 43.5, 39.7, 37.3, 36.3, 24.8, 22.7, 21.2.; HRMS (FAB) calcd. for C$_{25}$H$_{37}$N$_6$O$_5$ (M$^+$) 501.2826, found 501.2825.

Ionic liquid supported Leu-Phe-Gly-Gly-Boc-tyrosine 11: foam-like pale yellow solids; $^1$H NMR (400 MHz, Acetone-d$_6$) δ 9.08 (s, 1H), 8.21 (s, br, 1H), 8.07 (s, br, 1H), 7.80 (s, 1H), 7.68 (d, J=7.2 Hz, 1H), 7.67 (s, 1H), 7.56 (d, J=7.2 Hz, 1H), 7.34-7.20 (m, 5H), 7.15 (d, J=8.0 Hz, 2H), 6.90 (d, J=8.0 Hz, 2H), 6.49 (d, J=7.2 Hz, 1H), 4.76-4.56 (m, 3H), 4.54-4.51 (m, 2H), 4.40-4.33 (m, 2H), 4.08 (s, 3H), 3.96-3.66 (m, 4H), 3.31-2.91 (m, 4H), 1.85-1.70 (m, 2H), 1.62-1.55 (m, 1H), 1.36 (s, 9H), 1.30 (s, 9H), 0.94 (d, J=6.0 Hz, 3H), 0.89 (d, J=6.0 Hz, 3H); $^{13}$C NMR (100 MHz, Acetone-d$_6$) δ 174.0, 171.9, 171.7, 171.3, 169.8, 156.4, 154.5, 138.1, 137.8, 132.2, 129.9 (2C), 129.3 (2C), 128.6 (2C), 126.7, 124.1, 124.0 (2C), 122.9, 79.6, 77.9, 63.2, 57.2, 56.0, 51.4, 48.5, 44.0, 43.8, 39.8, 37.4, 37.0, 36.3, 28.6 (3C), 28.1 (3C), 24.8, 22.9, 21.2; HRMS (FAB) calcd. for C$_{43}$H$_{62}$N$_7$O$_9$ (M$^+$) 820.4605, found 820.4609.

Determination of the degree of racemization in the loading and peptide forming steps (if any).

Preparation of ionic liquid supported Leu-Phe-Boc 4a-d: 4a-d were prepared from the reactions of ionic liquid supported leucine 2a-b (L- and D-enantiomers) with Boc-L-phenylalanine and Boc-DL-phenylalanine using the general procedure as previously described. 4a: L, L-epimer, 4b: D, L-epimer, 4c: L, DL-epimers and 4d: D, DL-epimers.

Methyl N-(tert-Butyloxycarbonyl)-phenylalanyl-leucinate 5a-d: 4a (0.1 mmol), from the previous step, was dissolved in ammonia-saturated methanol (2 mL). The resulting solution was then stirred at room temperature overnight. After removing the solvent under reduced pressure, the residue was purified by flash column chromatography (silica gel 230-400 mesh, hexane-ethyl acetate gradient) to afford dipeptide product MeO-Leu(L)-Phe(L)-Boc 5a-(L, L). In the same manner, dipeptides MeO-Leu(D)-Phe(L)-Boc 5b-(D,L), MeO-Leu(L)-Phe(DL)-Boc 5c-(L,DL) and MeO-Leu(D)-Phe(DL)-Boc 5d-(D,DL) were also prepared. HPLC analysis: Diacel Chiralcel OD-H column, 5% isopropanol in hexane, 0.5 mL/min, λ=220 nm, $t_R$(L, L-epimer): 13.3 min, $t_R$(D, L-epimer): 13.4 min; $t_R$(L, D-epimer): 15.7 min; $t_R$(D, D-epimer): 22.2 min; Diacel Chiralcel OD-J column, 5% isopropanol in hexane, 0.3 mL/min, λ=220 nm, $t_R$(L, L-epimer): 16.0 min, $t_R$(D, L-epimer): 17.4 min.

MeO-Leu(L)-Phe(L)-Boc 5a-(L, L)[51]: white solids, m.p. 101-103° C. (lit.[17]: m.p. 101-104° C.). $^1$H NMR (400 MHz, Acetone-$d_6$) δ 7.52 (d, J=7.6 Hz, 1H), 7.26-7.18 (m, 5H), 6.07 (d, J=8.0 Hz, 1H), 4.56-4.50 (m, 1H), 4.42-4.38 (m, 1H), 3.68 (s, 3H), 3.20-2.88 (m, 2H), 1.75-1.68 (m, 1H), 1.62-1.58 (m, 2H), 1.35 (s, 9H), 0.92 (d, J=6.4 Hz, 3H), 0.91 (d, J=6.4 Hz, 3H). HPLC analysis showed no detectable amount of D, L-epimer, L, D-epimer and D, D-epimer.

MeO-Leu(D)-Phe(L)-Boc 5b-(D,L)[51]: colorless crystals, m.p. 136-138° C. $^1$H NMR (400 MHz, Acetone-$d_6$) δ 7.44 (d, J=7.2 Hz, 1H), 7.28-7.18 (m, 5H), 6.06 (d, J=8.0 Hz, 1H), 4.48-4.42 (m, 1H), 4.41-4.35 (m, 1H), 3.66 (s, 3H), 3.11-2.93 (m, 2H), 1.55-1.52 (m, 3H), 1.36 (s, 9H), 0.88 (d, J=6.4 Hz, 3H), 0.87 (d, J=6.4 Hz, 3H). HPLC analysis showed no detectable amount of L, L-epimer, L, D-epimer and D, D-epimer.

The peptide liberation (cleavage) step. To a mixture of the ionic liquid supported pentapeptide 11 (180 mg, 0.2 mmol) in THF/$H_2O$ (1:2, v/v, 3.0 mL) was added 1 M NaOH aqueous solution (0.2 mL). The mixture was stirred at room temperature for 5 h. The volatile component was removed under reduced pressure and the residue solution was acidified to pH 5-6. The precipitate was washed twice with distilled water and dried under vacuum to give 120 mg (85%) of Boc-pentapeptide 12 as foam-like pale yellow solid. $^1$H NMR (400 MHz, Acetone-$d_6$) δ 8.01 (s, br, 1H), 7.80 (s, br, 1H), 7.65 (d, J=6.8 Hz, 2H), 7.30-7.15 (m, 5H), 7.17 (d, J=8.0 Hz, 2H), 6.89 (d, J=8.0 Hz, 2H), 6.43 (d, J=7.2 Hz, 1H), 4.76-4.74 (m, 1H), 4.52-4.47 (m, 1H), 4.42-4.39 (m, 1H), 4.01-3.74 (m, 4H), 3.28-2.90 (m, 4H), 1.79-1.65 (m, 3H), 1.35 (s, 9H), 1.30 (s, 9H), 0.94 (d, J=6.0 Hz, 3H), 0.92 (d, J=6.0 Hz, 3H); $^{13}$C NMR (100 MHz, Acetone-$d_6$) δ 173.5, 173.2, 171.4, 170.0, 169.0, 156.1, 154.3, 138.0, 132.6, 130.0 (2C), 129.6 (2C), 128.4 (2C), 126.5, 124.0 (2C), 79.2, 77.8, 56.8, 54.9, 51.1, 43.5, 43.1, 40.8, 37.9, 37.3, 28.7 (3C), 28.2 (3C), 25.0, 23.0, 21.5; HRMS (FAB) calcd. for $C_{37}H_{53}N_5O_9Na$ (M+Na) 734.3741, found 734.3742.

The Boc-pentapeptide 12 (117 mg, 0.16 mmol) was dissolved in $CH_2Cl_2$ (1.5 mL), followed by the addition of TFA (1.5 mL) and several drops of anisole. The reaction mixture was stirred at ambient temperature under a nitrogen atmosphere for 0.5 h. Evaporation and washing with ether gave Leu$^5$-enkephalin as its TFA salt 14 (109 mg, 99%) as a pale yellow solid, m.p. 148-152° C. (authentic sample m.p. 150-153° C.); $[α]^{20}_D$=25.0 (c 0.8, 95% AcOH), authentic sample $[α]^{20}_D$=25.6 (c 0.9, 95% AcOH); HPLC $t_R$=16.0 min, (authentic sample $t_R$=15.7 min), Agilent Zorbax SB-CN Semi-prep column; eluent, 0-5 min, $H_2O$-0.05% TFA (v/v), 6-15 min, 0-60% $CH_3CN/H_2O$-0.05% TFA (v/v/v), 16-23 min, 60-100% $CH_3CN/H_2O$-0.05% TFA (v/v/v); post time, 7 min; flow rate, 3.0 ml/min; $^1$H NMR (400 MHz, Methanol-$d_4$) δ 7.24-7.21 (m, 4H), 7.18-7.15 (m, 1H), 7.08 (d, J=8.4 Hz, 2H), 6.77 (d, J=8.4 Hz, 2H), 4.71-4.67 (m, 1H), 4.42-4.39 (m, 1H), 4.07 (t, J=7.2 Hz, 1H), 3.96-3.72 (m, 4H), 3.19-2.92 (m, 4H), 1.71-1.61 (m, 3H), 0.94 (d, J=6.0 Hz, 3H), 0.90 (d, J=6.0 Hz, 3H); $^{13}$C NMR (100 MHz, Methanol-$d_4$) δ 175.1, 173.1, 171.0, 170.6, 170.4, 158.0, 138.0, 131.3 (2C), 130.2 (2C), 129.2 (2C), 127.5, 125.8, 116.8 (2C), 56.2, 55.6, 52.3, 43.9, 43.4, 41.7, 39.0, 37.7, 26.0, 23.2, 22.0; HRMS (FAB) calcd. for $C_{28}H_{37}N_5O_7Na$ (M+Na) 578.2592, found 578.2591.

Phenyl 2,3,4-tri-O-benzyl-1-thio-β-D-glucopyranoside (15): To a flask charged with phenyl 2,3,4-tri-O-benzyl-6-O-trimethylacetyl-1-thio-β-D-glucopyranoside (3.02 g, 4.82 mmol) was added a $NaOCH_3/HOCH_3$ solution (50 mL) and $CH_2Cl_2$ (15 mL) (pH=13). The solution was stirred at room temperature for 48 hours, evaporated to remove the solvent and dried in vacuo. Dry $CH_2Cl_2$ was added to the crude product residue and the insoluble salt was filtered off via Buchner funnel padded with filtering reagent, Celite™ 521. The filtrate was collected and the solvent was removed by rotatory evaporation and dried in vacuo to afford the product as a white solid (2.61 g, yield 100%); m.p. 127~129° C.; $^1$H NMR (400 MHz, $CDCl_3$), δ 7.51 (m, 2H), 7.40-7.27 (m, 18H), 4.94-4.85 (m, 4H), 4.77 (d, J=10 Hz, 1H), 4.73 (d, J=9.6 Hz, 1H), 4.66 (d, J=10.8 Hz, 1H), 3.89 (dd, J=2.8 Hz, 14.8 Hz, $H_{6a}$, 1H), 3.77-3.69 (m, 2H), 3.59 (t, J=8.8 Hz, 1H), 3.50 (t, J=8.8 Hz, 1H), 3.40 (m, 1H); $^{13}$C NMR (400 MHz, $CDCl_3$), δ 138.49, 138.09, 138.02, 133.67, 132.06, 129.25, 128.73-127.89 (m), 87.82, 86.84, 81.41, 79.61, 77.90, 76.13, 75.85, 75.43, 62.48; ESI-MS, calcd. for $C_{33}H_{34}SO_5$ (M+Na$^+$): m/z=565, found: 565.

Phenyl 2,3,4-tri-O-benzyl-6-O-bromoacetyl-1-thio-β-D-glucopyranoside (16a): To a solution of phenyl 2,3,4-tri-O-benzyl-1-thio-β-D-glucopyranoside (15) (0.988 g, 1.82 mmol) and bromoacetic acid (0.308 g, 2.21 mmol) in $CH_2Cl_2$ (40 mL) was added a 1.0 M solution of DCC (2.20 mL, 2.20 mmol) in $CH_2Cl_2$ and a small amount of DMAP (<5% equivalent to sugar). After being stirred at room temperature for 2 hours, the mixture was filtered to remove the side-product 1,3-dicyclohexylurea. The filtrate was evaporated to dryness and the residue subjected to flash column chromatography (silica gel 60 A, 230-400 mesh) using hexane and ethyl acetate (7:1, V/V) as the eluant to afford the pure product (1.08 g, yield 89%); m.p. 85~87° C.; $^1$H NMR (400 MHz, $CDCl_3$), δ 7.54 (m, 2H), 7.41-7.25 (m, 18H), 4.95-4.84 (m, 4H), 4.75 (d, J=10 Hz, 1H), 4.67 (d, J=9.6 Hz, 1H), 4.61 (d, J=10.8 Hz, 1H), 4.45 (dd, J=11.2 Hz, 0.8 Hz, 1H), 4.28 (m, 1H), 3.79 s, 2H), 3.73 (m, 1H), 3.55 (m, 2H), 3.51 (t, J=18.4 Hz, 1H); $^{13}$C NMR (300 MHz, $CDCl_3$), δ 166.91, 138.29, 138.02, 137.70, 133.51, 132.39, 129.14, 128.76-127.94 (m), 87.81, 86.96, 81.06, 77.49, 77.36, 76.19, 75.79, 75.38, 65.07, 25.90; ESI-MS, calcd. for $C_{35}H_{35}SO_6Br$ (M+Na$^+$): m/z=685, found: 685.

Phenyl 2,3,4-tri-O-benzyl-6-O-[2-(3-methyl-imidazolium)]acetyl-1-thio-β-D-glucopyranoside tetrafluoroborate (16b): To a solution of phenyl 2,3,4-tri-O-benzyl-6-O-bromoacetyl-1-thio-β-D-glucopyranoside (16a) (0.890 g, 1.34 mmol) in acetone (25 mL) was added a 1.0 M solution of 1-methylimidazole (1.61 mL, 1.61 mmol) in $CH_2Cl_2$ and then $NaBF_4$ (0.182 g, 1.66 mmol). After 72 hours of stirring at room temperature, the precipitate was filtered off and the filtrate was evaporated to dryness and dried in vacuo overnight. The product residue was washed three times with diethyl ether (15 mL) and the upper solvent was decanted.

The solid was dried in vacuo and the residue was further purified by adding 15 mL dry $CH_2Cl_2$ and then filtering off the precipitate. The filtrate was evaporated to dryness and dried in vacuo to afford the pure product as white foam (0.989 g, yield 98%); m. p. 42~44° C.; $^1H$ NMR (400 MHz, $CDCl_3$), δ 8.74 (s, 1H), 7.46 (m, 2H), 7.36-7.23 (m, 18H), 7.17 (m, 2H), 5.01-4.82 (m, 6H), 4.72 (d, J=10.0 Hz, 1H), 4.71 (d, J=9.6 Hz, 1H), 4.58 (d, J=11.2 Hz, 1H), 4.50 (dd, J=11.6 Hz, 2.4 Hz, 1H), 4.24 (dd, J=6.4 Hz, 12 Hz, 1H), 3.82 (s, 3H), 3.73 (m, 1H), 3.58 (m, 1H), 3.52-3.43 (m, 2H); $^{13}C$ NMR (300 MHz, $CDCl_3$), δ 165.90, 138.33, 138.07, 138.02, 137.83, 133.65, 131.58, 129.37, 128.76-127.92 (m), 123.69, 123.25, 87.41, 86.79, 81.02, 77.53, 76.74, 76.01, 75.70, 75.15, 65.51, 50.03, 36.81; ESI-MS calcd for the cation $C_{39}H_{41}SO_6N_2$ ($M^+$): m/z=665, found: 665.

Phenyl 2,3,4-tri-O-benzyl-6-O-[2-(3-methyl-imidazolium)]acetyl-1-thio-β-D-glucopyranosyl sulfoxide tetrafluoroborate (17b): To a solution of 16b (50.0 mg, 0.066 mmol) in $CH_2Cl_2$ (2 mL) at −78° C. was added m-chloroperoxybenzoic acid (m-CPBA) (15.0 mg, 0.066 mmol) in $CH_2Cl_2$ (1 mL) dropwise over 5 min. After 20 min of stirring at −78° C., the mixture was poured into an aqueous saturated $NaHCO_3$ solution (10 mL) with 15 mL $CH_2Cl_2$. The organic phase was separated, washed with aqueous saturated $NaHCO_3$ solution (10 mL) and dried over anhydrous $Na_2SO_4$. The solvent was removed by rotatory evaporation in vacuo. The product residue was further purified by washing with hexane and isopropyl ether (monitored by TLC) to afford the glycosyl sulfoxide as a white solid including two diastereomers (49.5 mg; yield 97%; ratio 60:40 for the two diastereomers as determined by NMR). $^1H$ NMR (400 MHz, $CDCl_3$), δ 9.08 (s, 1H), 7.54 (m, 2H), 7.40-7.16 (m, 20H), 5.11-4.20 (m, 11H), 3.97 (m, 2H), 3.91 (s, 2H), 3.90 (s, 1H), 3.85-3.26 (m, 2H); ESI-MS calcd. for the cation $C_{39}H_{41}SO_7N_2$ ($M^+$): m/z=681, found: 681.

Phenyl 2,3,4-tri-O-benzyl-6-O-[2-(3-methyl-imidazolium)]acetyl-β-D-glucopyranosyl-(1→6)-2,3,4-tri-O-benzyl-1-thio-β-D-glucopyranoside tetrafluoroborate (18b): To a solution of the monosaccharide sulfoxide bound to ionic liquid 17b (51.8 mg, 0.067 mmol; glycosyl donor), phenyl 2,3,4-tri-O-benzyl-1-thio-β-D-glucopyranoside (15, 114 mg, 0.21 mmol; glycosyl acceptor) and 2,6-di-tert-butyl-4-methylpyridine (58.8 mg, 0.286 mmol; acid scavenger) in $CH_2Cl_2$ (5 mL) at −78° C. was gradually added $Tf_2O$ (12 μL, 0.067 mmol) over 10 minutes via syringe. After 20 minutes of stirring at −78° C., the mixture was slowly warmed to 0° C. over one hour. The reaction was quenched by adding n-pentane (5 mL) which resulted in the appearance of a white precipitate. The mixture was cooled to −78° C. and the white precipitate was immediately removed by centrifugation. To the solution phase was added another portion of n-pentane (5 mL) followed by cooling to −78° C. The resulting precipitate was again removed by centrifugation. The solution phase was evaporated and the residue was washed with n-pentane for several times and then further washed with isopropyl ether until TLC analysis showed the residue was pure. The product (39 mg, yield 50%) was obtained as a white solid; m.p. 45-47° C.; $^1H$ NMR (400 MHz, $CDCl_3$), δ 9.10 (S, 1H), 7.51 (m, 2H), 7.41-7.13 (m, 35H), 5.10 (d, J=10.4 Hz, 1H), 5.00-4.52 (m, 15H), 4.41 (m, 1H), 4.19 (dd, J=12.4 Hz, 4.0 Hz, 1H), 3.99 (t, J=8.8 Hz, 1H), 3.90-3.75 (m, 6H), 3.73-3.62 (m, 2H), 3.55 (m, 2H), 3.42 (t, J=8.8 Hz, 1H), 3.29 (t, 1H); $^{13}C$ NMR (400 MHz, $CDCl_3$), δ=165.79, 138.78, 138.60, 138.41, 138.38, 138.20, 138.11, 138.03, 134.18, 131.78, 129.32, 128.73-127.69 (m), 123.65, 123.24, 97.30, 88.25, 86.81, 81.82, 81.31, 80.30, 79.06, 77.76, 77.57, 75.99, 75.89, 75.81, 75.25, 75.09, 72.83, 68.68, 66.89, 65.49, 50.51, 37.16; ESI-MS calcd. for the cation $C_{66}H_{69}SO_{11}N_2$ ($M^+$): m/z=1097, found: 1097.

Phenyl 2,3,4-tri-O-benzyl-6-O-[2-(3-methyl-imidazolium)]acetyl-β-D-glucopyranosyl-(1→6)-2,3,4-tri-O-benzyl-1-thio-β-D-glucopyranosyl sulfoxide tetrafluoroborate (19b): To a solution of the disaccharide sulfide 18b (56.1 mg, 0.047 mmol) in $CH_2Cl_2$ (2.5 mL) at −78° C. was added dropwise m-chloroperoxybenzoic acid (m-CPBA) (8.1 mg, 0.047 mmol) in $CH_2Cl_2$ (1 mL) over 5 min. After 20 min of stirring at −78° C. under the protection a nitrogen atmosphere, the mixture was poured into an aqueous saturated $NaHCO_3$ solution (10 mL) with $CH_2Cl_2$ (15 mL). The organic phase was separated, again washed with an aqueous saturated $NaHCO_3$ solution (10 mL) and dried over anhydrous $Na_2SO_4$. The solvent was removed by rotatory evaporation in vacuo. The product residue was further purified by washing with hexane and isopropyl ether (monitored by TLC), to afford the desired glycosyl sulfoxide as a white solid including two diastereomers (54.0 mg, yield 95%, ratio 60:40 for the two diastereomers as determined by NMR). $^1H$ NMR (400 MHz, $CDCl_3$), δ 9.48 (s, 1H), 7.58-7.13 (m, 37H), 5.00-4.40 (m, 18H), 3.95-3.25 (m, 13H); ESI-MS calcd. for the cation $C_{66}H_{69}SO_{12}N_2$ ($M^+$): m/z=1113, found: 1113.

Phenyl 2,3,4-tri-O-benzyl-6-O-[2-(3-methyl-imidazolium)]acetyl-β-D-glucopyranosyl-(1→6)-2,3,4-tri-O-benzyl-β-D-glucopyranosyl-(1-6)-2,3,4-tri-O-benzyl-1-thio-β-D-glucopyranoside tetrafluoroborate (20b): To a solution of the disaccharide sulfoxide bound to ionic liquid (19b; 45.1 mg; 0.038 mmol; glycosyl donor), phenyl 2,3,4-tri-O-benzyl-1-thio-β-D-glucopyranoside (15; 62.1 mg; 0.114 mmol; glycosyl acceptor) and 2,6-di-tert-butyl-4-methylpyridine (30.8 mg; 0.150 mmol; acid scavenger) in $CH_2Cl_2$ (5 mL) at −78° C. was gradually added $Tf_2O$ (6 μL, 0.036 mmol) over 10 min via syringe. After 20 min of stirring at −78° C., the mixture was slowly warmed to 0° C. over 1 hour. The reaction mixture was quenched by adding n-pentane (5 mL) which resulted in the appearance of a white precipitate. The reaction mixture was cooled to −78° C. and the precipitate was immediately removed by centrifugation. To the solution phase was added another portion of n-pentane (5 mL) followed by cooling to −78° C. The resulting precipitate was again removed by centrifugation. The solution phase was evaporated and the residue was washed several times with n-pentane and then further washed with isopropyl ether until TLC analysis showed the residue to be pure. The desired product (34 mg, yield 56%) was obtained as a white solid. $^1H$ NMR (400 MHz, $CDCl_3$), δ 9.04 (s, 1H), 7.51 (m, 2H), 7.42-7.17 (m, 48H), 7.05 (d, J=10.2 Hz, 2H), 5.00-4.50 (m, 25H), 4.39 (d, J=8.0 Hz, 1H), 4.15 (m, 1H), 4.00 (m, 2H), 3.89-3.72 (m, 6H), 3.70-3.30 (m, 8H), 3.25 (t, J=8.8 Hz, 1H); 13c NMR (400 MHz, $CDCl_3$), δ 165.77, 138.95-138.09 (m), 134.22, 131.87, 131.31, 129.29, 128.74-127.36 (m), 123.72, 123.76, 123.01, 103.91, 97.47, 97.26, 88.33, 87.74, 86.85, 84.88, 82.66-80.14 (m), 79.21, 79.06, 78.67, 77.54, 75.93-75.85 (m), 75.22-75.00 (m), 72.79, 72.72, 72.51, 70.86, 68.90, 69.58, 68.31, 66.44, 65.81, 65.53, 50.01, 36.90; ESI-MS calcd. for the cation $C_{93}H_{97}SO_{16}N_2$ ($M^+$): m/z=1529, found: 1529.

Cleavage of ionic liquid moiety from 20b to give the trisaccharide 21: To a flask charged with trisaccharide bound to ionic liquid (20b, 30.0 mg, 0.018 mmol) was added $Cs_2CO_3$ (6.1 mg, 0.018 mmol) and methanol (5 mL). After 12 hours of stirring at room temperature, the solvent was removed by rotatory evaporation and the residue dried in vacuo. To the residue was added dry $CH_2Cl_2$ (3 mL) and the insoluble salts were filtered off. The filtrate was evaporated to dryness and dried in vacuo to afford the desired product 21 (26.1 mg, yield 100%). $^1$H NMR (400 MHz, CDCl$_3$), δ 7.54 (m, 2H), 7.43-7.14 (m, 48H), 5.16 (d, J=3.2 Hz, 1H), 5.00-4.93 (m, 3H), 4.91-4.86 (m, 4H), 4.85-4.74 (m, 5H), 4.71-4.53 (m, 9H), 4.40 (d, J=8.0 Hz, 1H), 4.12 (d, J=10.0 Hz, 1H), 3.99 (m, 2H), 3.86-3.38 (m, 12H), 3.26 (m, 1H); $^{13}$C NMR (400 MHz, CDCl$_3$), δ 138.94-138.22 (m), 134.33, 132.01, 131.55, 129.19, 129.10, 128.59-127.44 (m), 103.91, 97.54, 97.31, 88.31, 87.79, 86.93, 84.81, 82.62, 81.95, 81.85, 81.75, 81.44, 81.33, 80.73, 80.63, 80.49, 79.23, 79.00, 78.12, 77.91, 77.75, 77.51, 75.95-75.80 (m), 75.45-75.25 (m), 72.75, 72.61, 72.57, 71.24, 68.65, 66.02, 65.52, 62.30; ESI-MS calcd. for C$_{87}$H$_{90}$SO$_{15}$Na (M+Na$^+$): m/z=1429, found: 1429.

Phenyl 2,3,4-tri-O-benzyl-6-O-acetyl-1-thio-β-D-glucopyranoside (16c): To a solution of phenyl-2,3,4-tri-O-benzyl-1-thio-β-D-glucopyranoside (15, 0.801 g, 1.48 mmol), dry pyridine (0.45 mL) and DMAP (less than 5% equivalent to sugar) in CH$_2$Cl$_2$ (9 mL) was added acetic anhydride (0.21 mL, 2.22 mmol). After 4 hours of stirring at room temperature under the protection of a nitrogen atmosphere, the reaction mixture was transferred into 150 mL of CH$_2$Cl$_2$, washed with aqueous 0.2 M HCl solution (30 mL), H$_2$O (30 mL), saturated aqueous NaHCO$_3$ solution (30 mL) and then brine (30 mL) respectively. The organic phase was dried over anhydrous Na$_2$SO$_4$ and the solvent was removed by rotatory evaporation to generate the crude product residue which was subjected to flash column chromatography (silica gel 60 A, 230-400 mesh) using hexane and ethyl acetate (5:1, V/V) as the eluant to afford the pure product (0.845 g, yield 98%); $^1$H NMR (400 MHz, CDCl$_3$), δ 7.55 (m, 2H), 7.40 (m, 2H), 7.36-7.25 (m, 16H), 4.95-4.84 (m, 4H), 4.75 (d, J=10 Hz, 1H), 4.67 (d, J=9.6 Hz, 1H), 4.58 (d, J=10.8, 1H), 4.37 (d, J=11.6 Hz, 1H), 4.22 (m, 1H), 3.73 (t, J=8.4 Hz, 1H), 3.55 (m, 2H), 3.50 (t, J=9.6 Hz, 1H), 2.11 (s, 3H); ESI-MS calcd. for C$_{35}$H$_{36}$SO$_6$Na (M+Na$^+$): m/z=607, found: 607.

Phenyl-2,3,4-tri-O-benzyl-6-O-acetyl-β-D-glucopyranosyl sulfoxide (17c): To a solution of 16c (1.01 g, 1.73 mmol) in-CH$_2$Cl$_2$ (5 mL) at −78° C. was added dropwise m-chloroperoxybenzoic acid (m-CPBA) (0.387 g, 1.73 mmol) in CH$_2$Cl$_2$ (7 mL) over 5 min. After 20 min of stirring at −78° C. under the protection of a nitrogen atmosphere, the mixture was poured into an aqueous saturated NaHCO$_3$ solution (100 mL) with CH$_2$CO$_2$ (50 mL). The organic phase was separated, washed again with an aqueous saturated NaHCO$_3$ solution (50 mL) and dried over anhydrous Na$_2$SO$_4$. The solvent was removed by rotatory evaporation in vacuo to provide the crude product residue which was subjected to flash column chromatography (silica gel 60 A, 230-400 mesh) using hexane and ethyl acetate (3:1, V/V) as an eluant system to afford the pure product as a mixture of two diastereomers (0.984 g, yield 95%, ratio 3:1 for the two diastereomers as determined by NMR); $^1$H NMR (400 MHz, CDCl$_3$), δ 7.62-7.16 (m, 20H), 5.06-4.78 (m, 6H), 4.59-4.36 (m, 2H), 4.19-3.30 (m, 8H); SI-MS calcd. for C$_{35}$H$_{36}$SO$_7$Na (M+Na$^+$): m/z=623, found: 623.

Phenyl 2,3,4-tri-O-benzyl-6-O-acetyl-β-D-glucopyranosyl-(1→6)-2,3,4-tri-O-benzyl-1-thio-β-D-glucopyranoside (18c): To a solution of the sulfoxide 17c (0.302 g, 0.503 mmol), phenyl 2,3,4-tri-O-benzyl-1-thio-β-D-glucopyranoside (15, 0.406 g, 0.754 mmol) and 2,6-di-tert-butyl-4-methylpyridine (0.315 g, 1.53 mmol) in CH$_2$Cl$_2$ (10 mL) at −78° C. was gradually added Tf$_2$O solution (0.09 mL, 0.503 mmol) in CH$_2$Cl$_2$ (5 mL) over 10 min via syringe. After 20 min of stirring at −78° C., the mixture was slowly warmed to −5° C. over 1.5 hours. The reaction was quenched by adding an aqueous saturated NaHCO$_3$ solution (6 mL) and partitioned between CH$_2$Cl$_2$ (35 mL) and aqueous saturated NaHCO$_3$ solution (20 mL). The organic phase was separated and further washed with aqueous saturated NaHCO$_3$ solution (40 mL). After drying over anhydrous Na$_2$SO$_4$, the organic phase was evaporated to dryness and the residue was subjected to flash column chromatography (silica gel 60A, 230-400 mesh) using hexane and ethyl acetate (6:1, 5:1, 4:1, V/V) as the eluant to afford the pure product as a colorless syrup (0.414 g, yield 81%). $^1$H NMR (400 MHz, CDCl$_3$), δ 7.54 (m, 2H), 7.42 (m, 2H), 7.38-7.24 (m, 31H), 5.05 (m, 2H), 4.94-4.56 (m, 12H), 4.25 (m, 2H), 4.02 (t, J=9.2 Hz, 1H), 3.92 (m, 1H), 3.86 (d, J=4.8 Hz, 1H), 3.80 (m, 1H), 3.75 (m, 1H), 3.70 (t, 1H), 3.62-3.46 (m, 3H), 3.28 (t, J=8.4 Hz, 1H), 2.03 (s, 3H); ESI-MS calcd for C$_{62}$H$_{64}$SO$_{11}$Na (M+Na$^+$): m/z=1039, found: 1039.

Phenyl 2,3,4-tri-O-benzyl-6-O-acetyl-β-D-glucopyranosyl-(1→6)-2,3,4-tri-O-benzyl-β-D-glucopyranosyl sulfoxide (19c): To a solution of the disaccharide sulfide 18c (0.202 g, 0.199 mmol) in CH$_2$Cl$_2$ (12 mL) at −78° C. was added dropwise m-chloroperoxybenzoic acid (m-CPBA) (0.045 g, 0.199 mmol) in CH$_2$Cl$_2$ (6 mL) over 5 min. After 20 min of stirring at −78° C. under the protection of a nitrogen atmosphere, the mixture was poured into an aqueous saturated NaHCO$_3$ solution (30 mL) together with CH$_2$Cl$_2$ (60 mL). The organic phase was separated, again washed with aqueous saturated NaHCO$_3$ solution (30 mL) and dried over anhydrous Na$_2$SO$_4$. The solvent was removed by rotatory evaporation in vacuo to provide the crude product residue which was subjected to flash column chromatography (silica gel 60 A, 230-400 mesh) using hexane and ethyl acetate (2:1, V/V) as the eluant system, affording the product as a mixture of two isomers (0.197 g, total yield 96%, ratio 4:1 for the two isomers as determined by NMR spectroscopy). First isomer, R$_f$=0.27 (2:1, hexanes/ethyl acetate, V/V); $^1$H NMR (400 MHz, CDCl$_3$), δ 7.60 (m, 2H), 7.46 (m, 4H), 7.42-7.22 (m, 29H), 5.05 (d, J=3.6 Hz, 1H), 5.00-4.66 (m, 12H), 4.60 (d, J=10.8 Hz, 1H), 4.27 (m, 2H), 3.87 (m, 3H), 3.74 (m, 4H), 3.59-3.47 (m, 3H), 3.35 (m, 1H) 2.07 (s, 3H); Second isomer, R$_f$=0.12 (2:1, hexanes/ethyl acetate, V/V); $^1$H NMR (400 MHz, CDCl$_3$), δ 7.51 (m, 2H), 7.39-7.19 (m, 31H), 7.06 (m, 2H), 4.98-4.88 (m, 3H), 4.82-4.52 (m, 10H), 4.43 (d, J=8.8 Hz, 2H), 4.25 (m, 2H), 4.39 (t, J=9.6 Hz, 1H), 3.90-3.69 (m, 6H), 3.60 (m, 1H), 3.49 (m, 2H), 2.05 (s, 3H). ESI-MS calcd. for C$_{62}$H$_{64}$SO$_{12}$Na (M+Na$^+$): m/z=1055, found: 1055.

Phenyl 2,3,4-tri-O-benzyl-6-O-acetyl-β-D-glucopyranosyl-(1→6)-2,3,4-tri-O-benzyl-β-D-glucopyranosyl-(1→6)-2,3,4-tri-O-benzyl-1-thio-β-D-glucopyranoside (19c): To a solution of sulfoxide 19c (0.110 g, 0.107 mmol), phenyl 2,3,4-tri-O-benzyl-1-thio-β-D-glucopyranoside (15, 0.088 g, 0.161 mmol) and 2,6-di-tert-butyl-4-methylpyridine (0.070 g, 0.34 mmol) in CH$_2$Cl$_2$ (6 mL) at −78° C., was gradually added Tf$_2$O (0.018 mL, 0.107 mmol) in CH$_2$Cl$_2$ (3 mL) over 10 min via syringe. After 20 min of stirring at −78° C., the mixture was slowly warmed to −15° C. over 1 hour, The reaction mixture was quenched by adding aqueous saturated NaHCO$_3$ (6 mL) and then partitioned between CH$_2$Cl$_2$ (30 mL) and aqueous saturated NaHCO$_3$ (15 mL). The organic phase was separated and further washed with aqueous saturated NaHCO$_3$ (20 mL). After drying over anhydrous Na$_2$SO$_4$, the organic phase was evaporated to dryness, and the crude residue subjected to flash column chromatography (silica gel 60A, 230-400 mesh) using hexane and ethyl acetate (4:1, V/V) as the eluant system to afford the product as a colorless syrup (0.132 g, yield 85%). $^1$H NMR (400 MHz, CDCl$_3$), δ 7.53 (m, 2H), 7.44-7.14 (m, 48H), 5.12 (d, J=3.2 Hz, 1H), 5.04-4.52 (m, 21H), 4.40 (m, 1H), 4.24-4.12 (m, 2H), 4.00 (m, 1H), 3.90-3.36 (m, 12H), 3.28 (m, 1H), 2.00 (s, 3H); $^{13}$C NMR (400 MHz, CDCl$_3$), δ 170.85, 138.99-138.14 (m), 134.27, 134.17, 132.06, 131.66, 129.24, 129.15, 128.64, 128.61-127.48 (m), 103.74, 97.51, 97.23, 88.37, 87.77, 86, 91, 86.86, 84.79, 82.59, 81.95, 81.86, 81.41, 81.23, 80.67, 80.36, 80.25, 79.16, 78.99, 78.02 77.56, 75.88 (m), 75.25 (m), 72.71, 72.49, 72.37, 71.02, 69.04, 68.30, 66.39, 65.94, 65.67, 63.47, 63.36, 21.34; ESI-MS calcd. for C$_{89}$H$_{92}$SO$_{16}$Na (M+Na$^+$): m/z=1471, found: 1471.

Phenyl 2,3,4-tri-O-benzyl-β-D-glucopyranosyl-(1→6)-2,3,4-tri-O-benzyl-β-D-glucopyranosyl-(1→6)-2,3,4-tri-O-benzyl-1-thio-β-D-glucopyranoside (21): To a flask charged with phenyl 2,3,4-tri-O-benzyl-6-O-acetyl-β-D-glucopyranosyl-(1→6)-2,3,4-tri-O-benzyl-β-D-glucopyranosyl-(1→6)-2,3,4-tri-O-benzyl-1-thio-β-D-glucopyranoside 20c (101 mg, 0.069 mmol) was added Cs$_2$CO$_3$ (22.4 mg, 0.069 mmol) and methanol (6 mL). After 14 hours of stirring at room temperature, the solvent was removed by rotatory evaporation and the crude residue dried in vacuo. To the residue was then added dry CH$_2$Cl$_2$ (3 mL) and the insoluble salts filtered off. The filtrate was evaporated to dryness and dried in vacuo to afford pure product (96.1 mg, yield 98%); R$_f$=0.28 (2:1, hexanes/ethyl acetate, V/V); $^1$H NMR (400 MHz, CDCl$_3$), δ 7.54 (m, 2H), 7.43-7.14 (m, 48H), 5.16 (d, J=3.2 Hz, 1H), 5.00-4.93 (m, 3H), 4.91-4.86 (m, 4H), 4.85-4.74 (m, 5H), 4.71-4.53 (m, 9H), 4.40 (d, J=8.0 Hz, 1H), 4.12 (d, J=10.0 Hz, 1H), 3.99 (m, 2H), 3.86-3.38 (m, 12H), 3.26 (m, 1H); $^{13}$C NMR (400 MHz, CDCl$_3$), δ 138.94-138.22 (m), 134.33, 132.01, 131.55, 129.19, 129.10, 128.59-127.44 (m), 103.91, 97.54, 97.31, 88.31, 87.79, 86.93, 84.81, 82.62, 81.95, 81.85, 81.75, 81.44, 81.33, 80.73, 80.63, 80.49, 79.23, 79.00, 78.12, 77.91, 77.75, 77.51, 75.95-75.80 (m), 75.45-75.25 (m), 72.75, 72.61, 72.57, 71.24, 68.65, 66.02, 65.52, 62.30; The sample for mass spectroscopy was filtered through silica gel to remove any cesium ion; ESI-MS calcd. for C$_{87}$H$_{90}$SO$_{15}$Na (M+Na$^+$): m/z=1429, found: 1429.

5'-O-Monomethoxytrityl-3'-O-succinyl-thymidine (23): Compound 22 (2.86 g, 5.56 mmol), succinic anhydride (1.67 g, 16.7 mmol), and DMAP (0.34 g, 2.78 mmol) were dissolved in anhydrous pyridine (20 mL) in an argon-purged, oven dried 50 mL flask. The reaction was allowed to stir for 2 days at room temperature. TLC analysis in dichloromethane:methanol 9:1 showed the complete disappearance of the starting material and the formation of a single, more polar product. The pyridine was removed under vacuum. The dark brown residue was then taken up in CH$_2$Cl$_2$ (100 mL) and washed with saturated brine. The organic phase was dried over Na$_2$SO$_4$ followed by removal of the solvent under vacuum; the product was obtained as a light brown foam in high yield (3.14 g, 92% yield). $^1$H NMR (DMSO-d$_6$) δ 11.39 & 8.30 (1H, s, NH), 7.50 (1H, s, CH), 7.37-7.21 (14H, m, Ar—H), 6.18 (1H, t, J=8 Hz, CH, H1'), 5.28 (1H, d, J=6 Hz, CH, H3'), 4.03 (1H, broad s, CH), 3.73 (3H, s, CH$_3$), 3.32-3.19 (2H, m, CH$_2$, H5'&5"), 2.62-2.61 (4H, unresolved m, 2 CH$_2$), 2.51-2.27 (2H, m, CH$_2$), 1.41 (3H, s, CH$_3$); C$_{34}$H$_{34}$N$_2$O$_9$Na$^+$ low resolution ESI-MS calculated 637.2, found: 637.1.

$^{MMT}$T$_{Succ-IL}$ (24): Compound 23 (1 g, 1.63 mmol), substituted imidazolium tetrafluoroborate 1 (0.38 g, 1.76 mmol), and DMAP (0.052 g, 0.41 mmol) were placed in a dry, nitrogen purged 100 mL round bottom flask. To this mixture dicyclohexylcarbodiimide (DCC) (0.68 g, 3.3 mmol) was added, followed by dry acetonitrile (20 mL). The reaction mixture was stirred for 3 days at room temperature. TLC analysis in 9:1 chloroform:methanol showed the formation of a more polar product that doesn't move from the base line. During the reaction the side product dicyclohexylurea (DCU) was formed as a white solid. When the reaction was stopped, DCU was allowed to settle and the reaction mixture was filtered through a scintered glass funnel and washed with acetonitrile several times. Further purification was achieved by adding the filtered solution dropwise to a stirred diethyl ether-ethyl acetate solution. The resulting precipitate, composed of underivatized ionic liquid 1 and the desired product 24, was then taken up in chloroform and extracted with water. The organic phase was dried over sodium sulphate and the solvent was evaporated and the product was dried under vacuum. The product 24 was obtained as a light brown foam (1.1 g, 83% yield). $^1$H NMR (Acetone-d6) δ 10.03 (1H, s, NH), 9.10 (1H, s, CH), 7.83 (1H, s, CH), 7.71 (1H, s, CH), 7.60 (1H, s, CH), 7.50-6.92 (14H, m, Ar—H), 6.33 (1H, t, J=8 Hz, CH, H1'), 5.50 (1H, d, J=6 Hz, CH, H3'), 4.55-4.51 (2H, m, CH$_2$), 4.70-4.66 (2H, m, CH$_2$), 4.15 (1H, broad s, CH), 4.05 (3, s, CH$_3$), 3.80 (3H, s, CH$_3$), 3.50-3.40 (2H, m, CH$_2$, H5'&5"), 2.70 (4H, broad s, 2 CH$_2$), 2.61-2.40 (2H, m, CH$_2$), 1.42 (3H, s, CH$_3$); C$_{40}$H$_{43}$N$_4$O$_9$$^+$ low resolution ESI-MS calculated 723.3, found: 723.4.

$^{HO}$T$_{Succ-IL}$ (25): To a solution of 24 (2.96 g, 3.65 mmol) in dichloromethane (200 mL) was added 3% trifluoroacetic acid in dichloromethane or acetonitrile (100 mL). During the addition of TFA, the solution became reddish orange and stirring was maintained for 20 minutes. The product was precipitated from 10% ethyl acetate/diethyl ether, filtered, redissolved in a minimum amount of the acid solution, precipitated again and filtered. The precipitate was rinsed with 10% ethyl acetate/diethyl ether, recovered from the filter by dissolving in acetonitrile and evaporated under reduced pressure, yielding compound 25 as a light brown foam (1.88 g, 96% yield). $^1$H NMR (DMSO-d$_6$) δ 11.40&11.39 (total of 1H, 2 s, NH), 9.10 (1H, s, CH), 7.76 (1H, s, CH), 7.72&7.45 (1H, s, CH), 7.70 (1H, s, CH), 6.15 (1H, m, CH, H1'), 5.27&5.19 (1H, m, CH, H3'), 4.60&3.60 (2H, m, CH$_2$, H5'&5"), 4.45 (2H, broad s, CH$_2$), 4.39 (2H, broad s, CH$_2$), 4.24-3.93 (1H, m, CH), 3.86 (3, s, CH$_3$), 2.61-2.60 (4H, unresolved m, 2 CH$_2$), 2.40-2.16 (2H, m, CH$_2$), 1.77 (3H, s, CH$_3$); C$_{20}$H$_{27}$N$_4$O$_8$$^+$ high resolution ESI-MS required 451.18289, found 451.18234.

$^{DMT}$ApT$_{Succ-IL}$ (27a): Compound 25 (0.12 g, 0.22 mmol), adenosine phosphoramidite 26a (0.33 g, 0.38 mmol), and dicyanoimidazole (0.33 g, 2.8 mmol) were transferred to a 50 mL oven dried, nitrogen purged round bottom flask. To the mixture was added dry THF or acetonitrile (5 mL) and the resulting solution was stirred at room temperature for 1-2 hours. The product was precipitated twice from 10% ethyl acetate/diethyl ether. At this point, the precipitate was redissolved in acetonitrile and 2,4,6-collidine or pyridine (approximately 300 µL) was added followed by addition of an aqueous iodine solution (0.1 M in THF/water 2:1, excess) to oxidize the phosphite triester intermediate. After 5 min the reaction mixture was quenched with an aqueous sodium bisulphate solution (9 mL), diluted with 90 mL CHCl$_3$ and extracted with 50 mL of water. The organic phase was dried over anhydrous Na$_2$SO$_4$ and evaporated under reduced pressure to yield a foam of 27a (0.259 g, 89%). $^{31}$P NMR (Acetonitrile-d3) δ –1.324, –1.477; C$_{61}$H$_{64}$N$_{10}$O$_{16}$P$^+$ low resolution ESI-MS calculated 1223.4, found 1223.4.

$^{DMT}$CpT$_{Succ-IL}$ (27b): Compound 25 (0.11, 0.20 mmol), cytidine phosphoramidite 26b (0.35 g, 0.41 mmol), and dicyanoimidazole (0.37 g, 3.1 mmol) were transferred to a 50 mL oven dried, nitrogen purged round bottom flask. The absence of solvent prevented any reaction from occurring. The reaction was commenced by injecting dry THF or acetonitrile (5 mL) into the flask and the solution was stirred at room temperature for 1-2 hours. The same workup was employed as in case of 27a and the product was obtained in high yield as a foam of 27b (0.234 g, 91%). $^{31}$P NMR (Acetonitrile-d3) δ −1.545, −1.754; $C_{60}H_{64}N_8O_{17}P^+$ low resolution ESI-MS calculated 1199.4, found 1199.4.

$^{DMT}GpT_{Succ-IL}$ (27c): Compound 25 (0.13 g, 0.24 mmol), guanosine phosphoramidite 26c (0.35 g, 0.42 mmol), and dicyanoimidazole (0.38 g, 3.2 mmol) were transferred to a 50 mL oven dried, nitrogen purged round bottom flask. The absence of solvent prevented any reaction from occurring. The reaction was commenced by injecting dry THF or acetonitrile (5 mL) into the flask and the solution was stirred at room temperature for 1-2 hours. The same workup was employed as in case of 27a and the product was obtained in high yield as a foam of 27c (0.214 g, 90%). $^{31}$P NMR (Acetonitrile-d3) δ −1.149, −1.194; $C_{58}H_{66}N_{10}O_{17}P^+$ low resolution ESI-MS calculated 1205.4, found 1205.6.

$^{DMT}TpT_{Succ-IL}$ (27d): Compound 25 (0.24 g, 0.45 mmol), thymidine phosphoramidite 26d (0.57 g, 0.77 mmol), and dicyanoimidazole (0.66 g, 5.6 mmol) were transferred to a 50 mL oven dried, nitrogen purged round bottom flask. The absence of solvent prevented any reaction from occurring. The reaction was commenced by injecting dry THF or acetonitrile (5 mL) into the flask and the solution was stirred at room temperature for 1-2 hours. The same workup was employed as in case of 27a and the product was obtained in high yield as a foam of 27d (0.492 g, 91%). $^{31}$P NMR (Acetonitrile-d3) δ −1.494, −1.584; $C_{54}H_{61}N_7O_{17}P^+$ low resolution ESI-MS calculated 1110.4, found 1110.4.

$^{HO}ApT_{Succ-IL}$ (28a): Compound 27a (0.26 g, 0.20 mmol) was dissolved in acetonitrile (1-2 mL) and 3% trifluoroacetic acid in acetonitrile (2-3 mL) was added. The reaction mixture was worked up following the same procedure as for 25 giving 28a as a foam in high yield (0.185 g, 93%). $^1$H NMR (Acetonitrile-d3) δ 6.47-6.51 (Ade H1'), 6.17-6.22 (Thy H1'), 5.25-5.30 (Ade and Thy H3'), 2.82-3.09 (Thy H5'&5"); 31P NMR (Acetonitrile-d3) δ −1.176, −1.516; $C_{40}H_{46}N_{10}O_{14}P^+$ high resolution ESI-MS required 921.29326, found 921.29271.

$^{HO}CpT_{Succ-IL}$ (28b): To a solution of 27b (0.23 g, 0.18 mmol) in acetonitrile (1-2 mL) was added 3% trifluoroacetic acid in acetonitrile (2-3 mL) to generate 28b. The reaction mixture was worked up following the same procedure as for 25 giving 28b as a foam in high yield (0.167 g, 95%). $^1$H NMR (Acetonitrile-d3) δ 6.09-6.24 (Cyt and Thy H1'), 5.21-5.33 (Thy H3'), 5.06-5.14 (Cyt H3'), 2.82-2.88 (Thy H5'&5"); $^{31}$P NMR (Acetonitrile-d3) δ −1.381, −1.613; $C_{39}H_{46}N_8O_{15}P^+$ high resolution ESI-MS required 897.28203, found 897.28148.

$^{HO}GpT_{Succ-IL}$ (28c): To a solution of 27c (0.21 g, 0.17 mmol) in acetonitrile (1-2 mL) was added 3% trifluoroacetic acid in acetonitrile (2-3 mL). The reaction mixture was worked up following the same procedure as for 25 giving 28c as a foam in high yield (0.157 g, 96%. $^1$H NMR (Acetonitrile-d3) δ 6.08-6.25 (Gua and Thy H1'), 5.26-5.30 (Gua H3'), 5.17-5.22 (Thy H3'), 2.81-3.05 (Thy H5'&5"); $^{31}$P NMR (Acetonitrile-d3) δ −1.047, −1.064; $C_{37}H_{48}N_{10}O_{15}P^+$ high resolution ESI-MS required 903.30382, found 903.30328.

$^{HO}TpT_{Succ-IL}$ (28d): To a solution of 27d (0.21 g, 0.18 mmol) in acetonitrile (1-2 mL) was added 3% trifluoroacetic acid in acetonitrile (2-3 mL). The reaction mixture was worked up following the same procedure as for 25 giving 28d as a foam in good yield (0.123 g, 78%). $^1$H NMR (Acetonitrile-d3) δ 6.16-6.24 (5'-Thy and 3'-Thy H1'), 5.22-5.30 (3'-Thy H3'), 5.07-5.12 (5'-Thy H3'), 2.30-2.86 (3'-Thy H5'&5"); $^{31}$P NMR (Acetonitrile-d3) δ −1.188, −1.284; $C_{33}H_{43}N_7O_{15}P^+$ high resolution ESI-MS required 808.25548, found 808.25493.

$^{DMT}TpTpT_{Succ-IL}$ (29): Compound 28d (0.065 g, 0.073 mmol) was mixed with 3'-phosphoramidite 26d (0.233 g, 0.31 mmol) and dicyanoimidazole (0.31 g, 2.6 mmol) in dry acetonitrile (5 mL) at room temperature. After being stirred for 2 h, the product was twice precipitated from 10% ethyl acetate/diethyl ether, oxidized and extracted in the same manner as for compounds 27a-d, to give compound 29 (104 mg, 92% yield) in high purity. $^{31}$P NMR (Acetonitrile-d3) −1.081, −1.194, −1.233, −1.262, −1.381, −1.403, −1.448, −1.477; $C_{67}H_{77}N_{10}O_{24}P_2^+$ low resolution ESI-MS calculated 1467.5, found 1467.8.

$^{HO}TpTpT_{Succ-IL}$ (30): To a solution of 29 in (97 mg, 0.06 mmol) in acetonitrile (1-2 mL) was added 3% trifluoroacetic acid in acetonitrile (2-3 mL). The reaction mixture was worked up following the same procedure as for 25 giving 30 as a glassy solid (77 mg, 98% yield). $^{31}$P NMR (Acetonitrile-d3) −1.157 to −1.531 (broad overlap of peaks); $C_{46}H_{59}N_{10}O_{22}P_2^+$ high resolution ESI-MS required 1165.32807, found 1165.32752.

$^{DMT}TpTpTpT_{Succ-IL}$ (31): Compound 30 (170 mg, 0.136 mmol) was mixed with 3'-phosphoramidite 26d (0.160 g, 0.215 mmol) and dicyanoimidazole (0.21 g, 1.8 mmol) in dry acetonitrile (5 mL) at room temperature. After being stirred for 2 h, the product was twice precipitated from 10% ethyl acetate/diethyl ether, oxidized and extracted in the same manner as for compounds 27a-d, to give compound 31 (231 mg, 89% yield) in high purity. $^{31}$P NMR (Acetonitrile-d3) −1.169 to −1.859 (broad overlap of peaks); $C_{80}H_{93}N_{13}O_{31}P_3^+$ low resolution ESI-MS calculated 1824.5, found 1824.2.

$^{HO}TpTpTpT_{Succ-IL}$ (32): To a solution of 31 (190 mg, 0.122 mmol) in acetonitrile (1-2 mL) was added 3% trifluoroacetic acid in acetonitrile (2-3 mL). The reaction mixture was worked up following the same procedure as for 25 giving compound 32 (160 mg, 99.9% yield). 31p NMR (Acetonitrile-d3) −1.142 to −1.51 (broad overlap of peaks); $C_{59}H_{75}N_{13}O_{29}P_3^+$ high resolution ESI-MS required 1522.40066, found 1522.40011.

Deprotection of oligonucleotides (33a-f): Removal of the cyanoethyl protecting group, the base protecting group (for a-c) and the succinyl linker to the ionic liquid support was achieved by treatment of 1-5 mg of compounds 28a-d, as well as compounds 30 and 32, with 1.5 mL of 3:1 concentrated ammonium hydroxide to absolute ethanol at 60° C. for 16 hours or at room temperature for 48 hours. After cooling the sample, the ammonia solution was evaporated and the residue was redissolved in water and purified by ion pairing reverse phase HPLC to obtain 33a-f.

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES

1) For a recent example of outstanding achievement in solution phase synthesis of oligosaccharides, see: Dudkin, V. Y.; Miller, J. S.; Danishefsky, S. J. *J. Am. Chem. Soc.* 2004, 126, 736.
2) Caruthers, M. H., Barone, A. D., Beaucage, S. L., Dodds, D. R., Fisher, E. F., McBride, L. J., Matteucci, M., Stabinsky, Z., Tang, J. Y. (1987) Chemical synthesis of deoxyoligonucleotides by the phosphoramidite method. *Methods Enzymol.*, 154, 287-313.
3) Alvarado-Urbina, G., Sathe, G. M., Liu, W. C., Gillen, M. F., Duck, P. D., Bender, R., Ogilvie, K. K. (1981) Automated synthesis of gene fragments. *Science*, 214, 270-274.
4) Ogilvie, K. K., Usman, N., Nicoghosian, K., Cedergren, R. J. (1988) Total chemical synthesis of a 77-nucleotide-long RNA sequence having methionine-acceptance activity. *Proc. Natl. Acad. Sci. U.S.A.*, 85, 5764-5768.
5) Damha, M. J., Ogilvie, K. K. (1993) Oligoribonucleotide synthesis. The silyl-phosphoramidite method. *Methods in molecular biology* (Clifton, N.J.), 20, 81-114.
6) Bellon, L., Wincott, F. (2000) Oligonucleotide synthesis. *Solid-Phase Synthesis*, 475-528.
7) Merrifield, R. B. Solid Phase Peptide Synthesis. I. The Synthesis of a Tetrapeptide. *J. Am. Chem. Soc.* 1963, 85, 2149-2154.
8) Letsinger, R. L., Mahadevan, V. (1965) Nucleotide chemistry. II. Oligonucleotide synthesis on a polymer support. *J. Am. Chem. Soc.*, 87, 3526-3527.
9) Letsinger, R. L., Hamilton, S. B. (1959) Organoboron compounds. X. Popcorn polymers and highly cross-linked vinyl polymers containing boron. *J. Am. Chem. Soc.*, 81, 3009-3012.
10) Bayer, E., Mutter, M. (1972) Liquid phase synthesis of peptides. *Nature*, 237, 512-513.
11) Bonora, G. M., Scremin, C. L., Colonna, F. P., Garbesi, A. (1990) HELP (high efficiency liquid phase) new oligonucleotide synthesis on soluble polymeric support. *Nucleic Acids Res.*, 18, 3155-3159.
12) Douglas, S. P.; Whitfield, D. M.; Krepinsky, J. J. Polymer-Supported Solution Phase Synthesis of Oligosaccharides. *J. Am. Chem. Soc.* 1991, 113, 5095-5097; *J. Am. Chem. Soc.* 1995, 117, 2116.
13) Seeberger, P. H.; Danishefsky, S. J. *Acc. Chem. Res.* 1998, 31, 685.
14) Plante, O. J.; Palmacci, E. R.; Seeberger, P. H. *Science* 2001, 291, 1523.
15) Sears, P.; Wong, C.-H. *Science* 2001, 291, 2344.
16) Jaunzems, J.; Hofer, E,; Jesberger, M.; Sourkouni-Argirusi, G.; Kirschning, A. *Angew. Chem. Int Ed.* 2003, 42, 1166.
17) a) Seeberger, P. H.; Haase, W. C. Chem. Rev. 2000, 100, 4349. b) Osborn, H. M. I.; Khan, T. H. *Tetrahedron* 1999, 55,1807.
18) Love, K. R.; Seeberger, P. H. Automated Solid-Phase Synthesis of Protected Tumor-Associated Antigen and Blood Group Determinant Oligosaccharides. *Angew. Chem. Int Ed.* 2004, 43, 602-605.
19) a) Mutter, M.; Hagenmaier, H.; Bayer, E. *Angew. Chem. Int Ed.* 1971, 10, 811-812; b) Bayer, E.; Mutter, M. *Nature* 1972, 237, 512-513.
20) Jiang, L.; Hartly, R. C.; Chan, T.-H. *Chem. Comm.* 1996, 2193.
21) Ito, Y.; Ogawa, T. *J. Am. Chem. Soc.* 1997, 119, 5562.
22) Wentworth, Jr. P.; Janda, K. D. *Chem. Comm.* 1999, 1918.
23) Majumdar, D.; Zhu, T.; Boons, G.-J. *Org. Lett* 2003, 5, 3591.
24) For reviews, see: a) Gravert, D. J.; Janda, K. D. Soluble Polymer-Supported Organic Synthesis. *Chem. Rev.* 1997, 97, 489-509; b) Toy, P. H.; Janda K. D., *Acc. Chem. Res.* 2000, 33, 546-554.
25) (a) Horvath, I. T.; Rabai, J. *Science* 1994, 266, 72-75; (b) Studer, A.; Hadida, S.; Ferritto, R.; Kim, S.-Y.; Jeger, P.; Wipf, P.; Curran, D. P. Fluorous Synthesis: A Fluorous Phase Strategy for Improving Separation Efficiency in Organic Synthesis. *Science* 1997, 275, 823-826; (c) Horvath, I. T. Fluorous Biphase Chemistry. *Acc. Chem. Res.* 1998, 31, 641-650; (d) Wende, M.; Meier, R.; Gladysz, J. A. *J. Am. Chem. Soc.* 2001, 123, 11490-11491; (e) Wende, M.; Gladysz, J. A. *J. Am. Chem. Soc.* 2003, 125, 5861-5872; (f) Zhang, W. *Tetrahedron* 2003, 59, 4475; (g) Betzemeier, B.; Knochel, P. *Angew. Chem., Int Ed. Engl.*, 1997, 36, 2623-2624.
26) a) Curran, D. P.; Ferrito, R.; Hua, Y. *Tetrahedron Lett* 1998, 39, 4937. b) Miura, T.; Goto, K.; Hosaka, D.; Inazu, T. Oligosaccharide Synthesis on a Fluorous Support. *Angew. Chem. Int Ed.* 2003, 42, 2047-2051. c) Miura, T.; Hirose, Y.; Ohmae, M.; Inazu, T. *Org. Lett.* 2001, 3, 3947. d) Miura, T.; Inazu, T. *Tetrahedron Lett.* 2003, 44, 1819. e) Jing, Y. Huang, X. *Tetrahedron Lett.* 2004, 45, 4615. f Manzoni, L. *Chem. Comm.* 2003, 2930. g) Manzoni, L.; Castelli, R. *Org. Lett* 2004, 6, 4195. h) Palmacci, E. R.; Hewitt, M. C.; Seeberger, P. H. *Angew. Chem. Int Ed.* 2001, 40, 4433.
27) a) Mizuno, M.; Goto, K.; Miura, T.; Hosaka, D.; Inazu, T. *Chem. Commun.* 2003, 972-973; b) Mizuno, M.; Goto, K.; Miura, T.; Matsuura, T.; Inazu, T. Peptide Synthesis on Fluorous Support. *Tetrahedron Lett.* 2004, 45, 3425-3428.
28) a) Miura, T.; Hirose, Y.; Ohmae, M.; lnazu, T. *Org. Lett.* 2001, 3, 3947-3950; b) Miura, T.; Inazu, T. *Tetrahedron Lett.* 2003, 44, 1819-1821; c) Miura, T.; Goto, K.; Hosaka, D.; Inazu, T. *Angew. Chem. Int. Ed.* 2003, 42, 2047-2051.
29) For recent reviews on ionic liquids, see: a) Wasserscheid, P.; Keim, W. *Angew. Chem. Int. Ed.* 2000, 39, 3773. b) Welton, T. *Chem. Rev.* 1999, 99, 2071. c) Sheldon, R. *Chem. Comm.* 2001, 2399. d) Wilkes, J. S. *Green Chem.* 2002, 4, 73; e) Wasserscheid, P.; Welton, T. Ionic Liquids in Synthesis, Wiley-V C H, Weinheim, Germany, 2003; (f) Holbrey, J. D., Seddon, K. R. *J. Chem. Soc., Dalton Trans.* 1999, 2133-2140.
30) a) Sheldon, R. *Chem. Commun.* 2001, 2399-2407; b) Sheldon, R. A.; Lau, R. M.; Sorgedrager, M. J.; Rantwijk, F. V.; Seddon, K. R. Biocatalysis in Ionic Liquids. *Green Chem.* 2002, 4, 147-151.
31) a) Fuller, J., Carlin, R. T., Osteryoung, R. A. *J. Electrochem. Soc.* 1997, 144, 3881-3886; b) Fuller, J., Breda, A. C., Carlin, R. T. (1998) *J. Electroanal. Chem.*, 1998, 459, 29-34.
32) a) Huddleston, J. G., Rogers, R. D. *Chem. Commun.* 1998, 1765-1766; b) Boesmann, A., Datsevich, L., Jess, A., Lauter, A., Schmitz, C., Wasserscheid, P. *Chem. Commun.* 2001, 2494-2495.
33) Ye, C., Liu, W., Chen, Y., Yu, L. *Chem. Commun.* 2001, 2244-2245.
34) Kimizuka, N.; Nakashima, T. Spontaneous Self-Assembly of Glycolipid Bilayer membranes in Super-Phylic Ionic Liquid and Formation of Ionogel. *Langmuir* 2001, 17, 6759-6761; b) For other ionic liquids containing PEG, see Leone, A. M.; Weatherly, S. C.; Williams, M. E.; Thorp, H. H.; Murray, R. W. *J. Am. Chem. Soc.* 2001, 123, 218-222.

35) a) Fraga-Dubreuil, J.; Bazureau, J. P. *Tetrahedron Lett* 2001, 42, 6097-6100; b) Fraga-Dubreuil, J.; Bazureau, J. P. *Tetrahedron* 2003, 59, 6121-6130; c) Handy, S. T.; Okello, M. *Tetrahedron Lett.* 2003, 44, 8399-8402; d) Miao, W.; Chan, T. H. *Org. Lett.* 2003, 5, 5003-5005; e) Anjaiah, S.; Chandrasekhar, S.; R. Gree, *Tetrahedron Lett.* 2004, 45, 569-571; f) de Kort, M.; Tuin, A. W.; Kuiper, S.; Overkleeft, H. S.; van der Marel, G. A.; Buijsman, R. C. *Tetrahedron Lett.* 2004, 45, 2171-2175; g) Law, M. C.; Wong, K.-Y.; Chan, T. H. *J. Org. Chem.* 2005, 70, 10434.

36) a) Audic, N.; Clavier, H.; Mauduit, M.; Guillemin, J.-C. *J. Am. Chem. Soc.* 2003, 125, 9248-9249; b) Yao, Q.; Zhang, Y. *Angew. Chem. Int. Ed.* 2003, 42, 3395-3398.

37) Peptide synthesis using ionic liquids as reaction media has been reported. See: Vallette, H.; Ferron, L.; Coquerel, G.; Gaumont, A.-C.; Plaquevent, J.-C. *Tetrahedron Lett.* 2004, 45, 1617-1619.

38) Bower, J. D.; Guest, K. P.; Morgan, B. A. *J. Chem. Soc. Perkin Trans.* 1, 1976, 2488.

39) Miao, W.; Chan, T. H. *J. Org. Chem.* 2005, 70, 3251.

40) For a recent monograph on peptide synthesis, see Lloyd-Williams, P.; Albericio, F.; Giralt, E. *Chemical Approaches to the Synthesis of Peptides and Proteins*, CRC Press, Boca Raton, 1997.

41) An authentic sample of Leu[5]-enkephalin was purchased from Sigma-Aldrich Canada Ltd. and was reported to be 97% pure.

42) HPLC conditions: column, Agilent Zorbax SB-CN Semi-prep (9.4×250 mm); eluent, 0-5 min, $H_2O$-0.05% TFA (v/v), 6-15 min, 0-60% $CH_3CN/H_2O$-0.05% TFA (v/v/v), 16-23 min, 60-100% $CH_3CN/H_2O$-0.05% TFA (v/v/v); post time, 7 min; flow rate, 3.0 ml/min.

43) Jiang, L.; Chan, T. H. *J. Org. Chem.* 1998, 63, 6035.

44) a) Kahne, D.; Walker, S.; Cheng, Y.; Van, D. E. *J. Am. Chem. Soc.* 1989, 111, 6881. b) Yan, L.; Kahne, D. *J. Am. Chem. Soc.* 1996,118, 9239. c) Gildersleeve, J.; Pascal, Jr. R. A.; Kahne, D. *J. Am. Chem. Soc* 1998, 120, 5961. d) Gildersleeve, J.; Smith, A.; Sakurai, K.; Raghavan, S.; Kahne, D. *J. Am. Chem. Soc.* 1999, 121, 6176. e) Liang, R.; Yan, L.; Leobach, J.; Ge, M.; Uozumi, Y.; Sekanina, K.; Horan, N.; Gildersleeve, J.; Thompson, C.; Smith, A.; Biswas, K.; Still, W. C.; Kahne, D. *Science* 1996, 274, 1520.

45) a) Crich, D.; Sun, S. *J. Org. Chem.* 1997, 62, 198. b) Crich, D.; Smith, M. *J. Am. Chem. Soc.* 2002, 124, 8867. c) Crich, D.; de la Mora, M.; Vinod, A. U. *J. Org. Chem.* 2003, 68, 8142.

46) a) Garcia, B.; Poole, J. L.; Gin, D. Y. *J. Am. Chem. Soc.* 1997, 119, 7597. b) Honda, E.; Gin, D. Y. *J. Am. Chem. Soc.* 2002, 124, 7342. c) Wipf, P.; Reeves, J. T. *J. Org. Chem.* 2001, 66, 7910.

47) Guillier, F.; Orain, D.; Bradley, M. *Chem. Rev.* 2000, 100, 2091.

48) Usman, N., Ogilvie, K. K., Jiang, M. Y., Cedergren, R. J. *J. Am. Chem. Soc.* 1987, 109, 7845-7854.

49) Damha, M. J., Ogilvie, K. K. *J. Org. Chem.* 1988, 53, 3710-3722.

50) Hadden, C. E., Martin, G. E., Krishnamurthy, V. V. *Magn. Reson. Chem.* 2000, 38, 143-147.

51) Backes, B. J.; Virgilio, A. A.; Ellman, J. A. *J. Am. Chem. Soc.* 1996, 118, 3055-3056.

---

---

What is claimed is:

1. A method of synthesizing an oligomer comprising:
   a) contacting a monomer unit of an amino acid, a saccharide, or a nucleotide or nucleoside with an ionic liquid-support compound, to form an ionic liquid-supported monomer, wherein the ionic liquid-supported monomer comprises the ionic liquid-support compound covalently bonded to the monomer unit, wherein the ionic liquid-support compound is an organic salt comprising a heterocyclic or substituted heterocyclic quaternary nitrogen-containing organic cation, a heterocyclic or substituted heterocyclic quaternary phosphonium containing organic cation, or a heterocyclic or substituted heterocyclic trivalent sulfonium containing organic cation, and an anion balancing the charge on said organic cation;

b) contacting the ionic liquid-supported monomer with at least one further monomer unit of an amino acid, a saccharide, or a nucleotide at reaction conditions to provide an ionic liquid-supported oligomer that comprises the ionic liquid-support compound covalently bonded to an oligopeptide, oligosaccharide, or an oligonucleotide, wherein said ionic liquid-supported monomer and said at least one further monomer unit are solubilized in an organic solvent during said contacting;

c) optionally, contacting the ionic liquid-supported oligomer with at least one further monomer unit of an amino acid, a saccharide, or a nucleotide at reaction conditions; and d) cleaving the ionic liquid-support compound from the ionic liquid-supported oligomer.

2. The method of claim 1, further comprising repeating step c), a select number of times to yield a desired ionic liquid-supported oligomer.

3. The method of claim 2, further comprising isolating the oligomer from the ionic liquid-support compound.

4. The method of claim 1, wherein the organic cation is selected from the group consisting of N-substituted pyridine and 1,3-disubstituted imidazole.

5. The method of claim 1, wherein the anion is selected from the group consisting of $Cl^-$, $Br^-$, $BF_4^-$, $PF_6^-$, $SbF_6^-$, $CuCl_2^-$, and $AlCl_4^-$.

6. The method of claim 1, wherein the monomer units are amino acids.

7. The method of claim 1, wherein the monomer units are nucleotides.

8. The method of claim 1, wherein the monomer units are saccharides.

9. The method of claim 6, wherein the oligomer comprises from 2 to 15 monomer units.

10. The method of claim 9, wherein the oligomer comprises from 2 to 10 monomer units.

11. The method of claim 10, wherein the oligomer comprises from 2 to 5 monomer units.

12. The method of claim 1, wherein the ionic liquid-supported oligomer produced is solubilized in a polar organic solvent.

13. The method of claim 12, wherein the oligomer is detached from the ionic liquid-supported compound and then separated from the polar organic solvent.

14. The method of claim 1, wherein the oligomer is $Leu^5$-enkephalin.

* * * * *